(12) United States Patent
Simpson et al.

(10) Patent No.: US 11,565,260 B2
(45) Date of Patent: *Jan. 31, 2023

(54) MULTI-CHAMBERED ASSAY DEVICES AND ASSOCIATED METHODS, SYSTEMS AND APPARATUSES THEREOF FOR DETECTION OF ANALYTES

(71) Applicant: Orbis Diagnostics Limited, Auckland (NZ)

(72) Inventors: Miriam Cather Simpson, Auckland (NZ); Matheus Jose Teixeira Vargas, Auckland (NZ); Mithileshwari Chandrasekhar, Auckland (NZ); David Edward Williams, Auckland (NZ)

(73) Assignee: Orbis Diagnostics Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,219

(22) Filed: May 13, 2022

(65) Prior Publication Data

US 2022/0274110 A1 Sep. 1, 2022

Related U.S. Application Data

(63) Continuation of application No. PCT/US2021/023523, filed on Mar. 22, 2021.
(Continued)

(51) Int. Cl.
*B01L 3/00* (2006.01)
*G01N 33/543* (2006.01)
(Continued)

(52) U.S. Cl.
CPC ... *B01L 3/502761* (2013.01); *B01L 3/502715* (2013.01); *G01N 33/543* (2013.01);
(Continued)

(58) Field of Classification Search
CPC .......... B01L 3/502761; B01L 2400/06; B01L 3/502715; B01L 2400/0487;
(Continued)

(56) References Cited

U.S. PATENT DOCUMENTS 3,744,975 A 7/1973 Mailen
4,470,954 A 9/1984 Chiknas
(Continued)

FOREIGN PATENT DOCUMENTS

JP 2007330857 A 12/2007

OTHER PUBLICATIONS

International Search Report and Written Opinion issued for the International Application No. PCT/US2021/023523, dated Aug. 6, 2021 (9 pages).
(Continued)

*Primary Examiner* — Brian J. Sines
(74) *Attorney, Agent, or Firm* — Cooley LLP; Matthew Pavao; Brian P. Hopkins

(57) ABSTRACT

Accordingly, in some embodiments of the disclosure, a multi-chambered assay device is provided, which is configured for arrangement on a disc, as well as configured to process an individual sample. A plurality of such assay devices can be arranged along a periphery of the disc at a distance/radius from the center, such that a plurality of individual samples can be processed, e.g., one per assay device. In addition, in an arrangement that a plurality of assay devices are used, they can be spaced apart such that they balance the disc during rotation (which can be with samples contained in one or more of the assay devices, a plurality, a majority, or all of the assay devices).

28 Claims, 17 Drawing Sheets

Related U.S. Application Data

(60) Provisional application No. 63/005,816, filed on Apr. 6, 2020, provisional application No. 62/992,566, filed on Mar. 20, 2020, provisional application No. 62/992,561, filed on Mar. 20, 2020.

(51) Int. Cl.
   *G01N 33/74* (2006.01)
   *G01N 21/65* (2006.01)

(52) U.S. Cl.
   CPC .... *G01N 33/743* (2013.01); *B01L 2200/0668* (2013.01); *B01L 2200/16* (2013.01); *B01L 2300/0654* (2013.01); *B01L 2300/0803* (2013.01); *B01L 2400/0487* (2013.01); *B01L 2400/06* (2013.01); *G01N 21/65* (2013.01)

(58) Field of Classification Search
   CPC ..... B01L 2200/0668; B01L 2300/0803; B01L 2200/16; B01L 2300/0654; G01N 33/543; G01N 33/743
   See application file for complete search history.

(56) References Cited

U.S. PATENT DOCUMENTS

| | | | |
|---|---|---|---|
| 4,673,653 A | 6/1987 | Guigan | |
| 4,938,927 A | 7/1990 | Kelton et al. | |
| 5,061,446 A | 10/1991 | Guigan | |
| 5,242,803 A | 9/1993 | Burtis et al. | |
| 5,281,539 A * | 1/1994 | Schramm | G01N 33/743 436/806 |
| 6,670,115 B1 * | 12/2003 | Zhang | G01N 33/5438 436/538 |
| 9,897,596 B2 | 2/2018 | Kellogg et al. | |
| 2002/0185184 A1 * | 12/2002 | O'Connor | B01F 33/30 137/822 |
| 2005/0249641 A1 | 11/2005 | Blankenstein et al. | |
| 2006/0141529 A1 * | 6/2006 | Koleske | C12N 9/1211 435/7.1 |
| 2009/0111197 A1 | 4/2009 | Khan et al. | |
| 2011/0088786 A1 | 4/2011 | Blankenstein et al. | |
| 2012/0312687 A1 * | 12/2012 | Miller | B01D 65/02 977/773 |
| 2013/0295593 A1 * | 11/2013 | Beckert | C07K 14/47 530/391.1 |
| 2014/0134631 A1 | 1/2014 | Clime et al. | |
| 2014/0242721 A1 | 8/2014 | Kellogg et al. | |
| 2015/0316542 A1 | 11/2015 | Curtin | |
| 2019/0314813 A1 | 10/2019 | Doolan et al. | |

OTHER PUBLICATIONS

CAS 54827-17-7 "Tetramethylbenzidine", 2017, 6 pages.
Gubala et al. "Point of Care Diagnostics: Status and Future", Analytical Chemistry, 2012, vol. 84, p. 487-515.

* cited by examiner

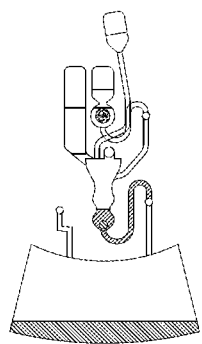
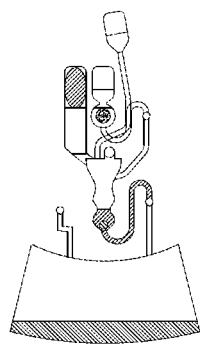
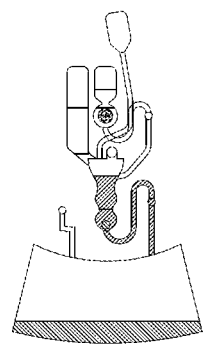
FIG. 3J    FIG. 3K    FIG. 3L
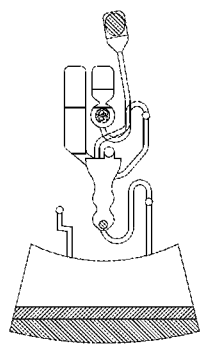
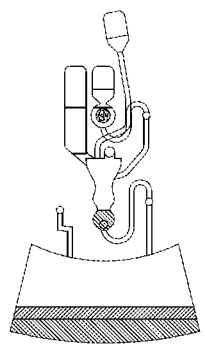
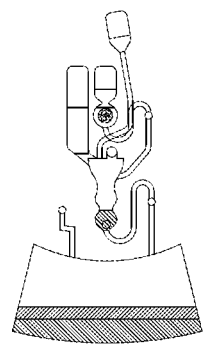
FIG. 3M    FIG. 3N    FIG. 3O

| E.g.,Task | See Fig. | Mode | Speed (RPM) | Acceleration (RPM/s) | Duration (s) | Add solution before next task |
|---|---|---|---|---|---|---|
| 1 | Fig. 3A | Clockwise spin | 500 | 500 | 2 | x (sample) |
| 2 | Fig. 3A-B | Clockwise spin | 2000 | 500 | 3 | |
| 3 | Fig. 3C | Mix | 550 | 2500 | 270 | x (WB) |
| 4 | Fig. 3D | Clockwise spin | 500 | 500 | 1 | |
| 5 | Fig. 3D-E | Clockwise spin | 3000 | 500 | 6 | x (WB) |
| 6 | Fig. 3D | Clockwise spin | 500 | 500 | 1 | |
| 7 | Fig. 3D-E | Clockwise spin | 3000 | 750 | 6 | x (Secondary buffer) |
| 8 | Fig. 3F-G | Clockwise spin | 500 | 500 | 2 | |
| 9 | Fig. 3H | Mix | 550 | 2500 | 75 | |
| 10 | Fig. 3I | Clockwise spin | 4000 | 250 | 15 | |
| 11 | Fig. 3J | Mix | 550 | 2500 | 270 | X(WB) |
| 12 | Fig. 3K | Clockwise spin | 500 | 500 | 1 | |
| 13 | Fig. 3L | Clockwise spin | 2000 | 500 | 6 | X(WB) |
| 14 | Fig. 3K | Clockwise spin | 500 | 500 | 1 | |
| 15 | Fig. 3L | Clockwise spin | 3600 | 1200 | 6 | X(WB) |
| 16 | Fig. 3K | Clockwise spin | 500 | 500 | 1 | |
| 17 | Fig. 3L | Clockwise spin | 3000 | 1000 | 6 | X(colorimetric reagent) |
| 18 | Fig. 3M-N | Clockwise spin | 2000 | 500 | 4 | |
| 19 | Fig. 3O | Mix | 550 | 2500 | 240 | |

*FIG. 4*

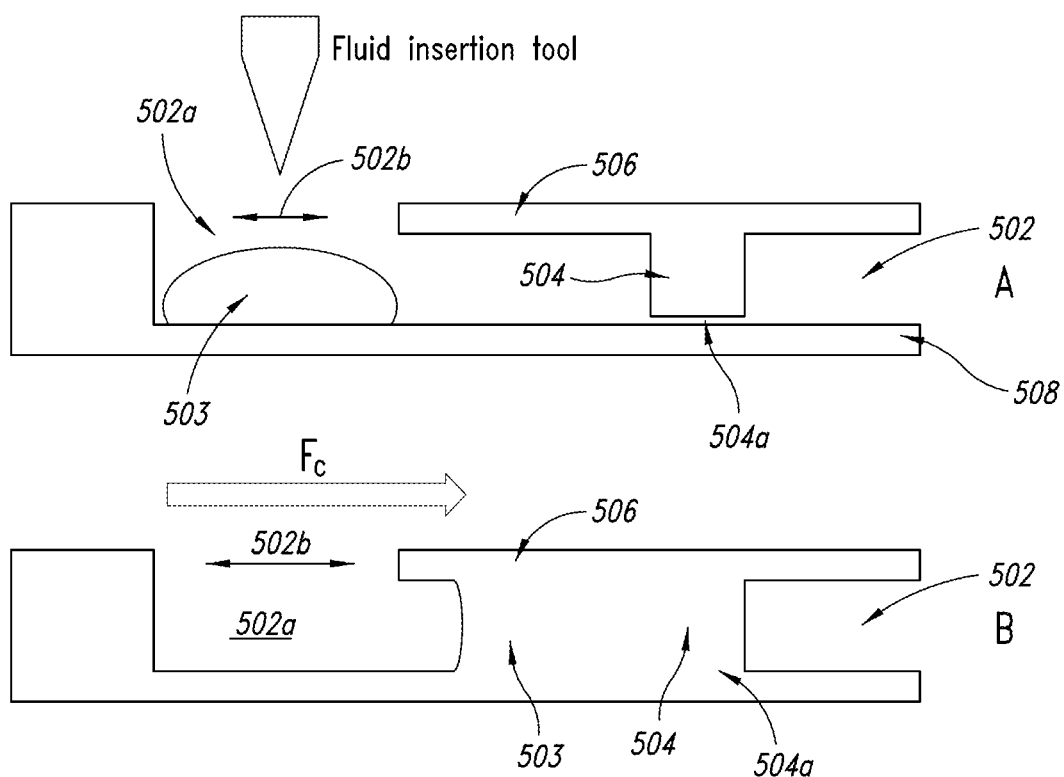
*FIG. 5A*  *FIG. 5B*
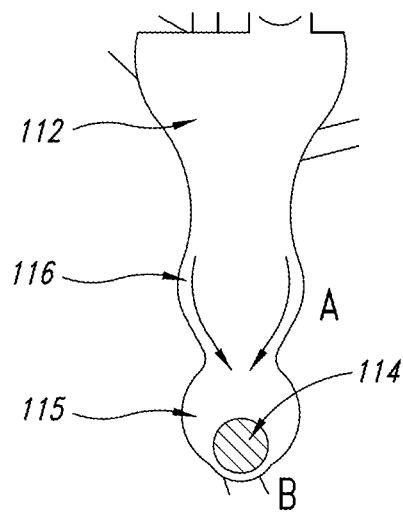
*FIG. 6*

MULTI-CHAMBERED ASSAY DEVICES AND ASSOCIATED METHODS, SYSTEMS AND APPARATUSES THEREOF FOR DETECTION OF ANALYTES

RELATED APPLICATIONS

This application is a continuation of international application no. PCT/US2021/023523, entitled, "SYSTEMS, DEVICES AND METHODS FOR FLUIDIC HEIGHT CONTROL FOR A MICROFLUIDIC CHIP," filed Mar. 22, 2021, which claims benefit of and priority to U.S. provisional patent application nos. 62/992,566, entitled, "SYSTEMS, DEVICES AND METHODS FOR FLUIDIC HEIGHT CONTROL FOR A MICROFLUIDIC CHIP," filed Mar. 20, 2020, 62/992,561, entitled, "SYSTEMS, DEVICES AND METHODS FOR MICROFLUIDIC CENTRIFUGE MIXING," filed Mar. 20, 2020, and 63/005,816, entitled, "METHODS, SYSTEMS AND DEVICE FOR BEAD DETECTION OF ANALYTES IN MICROFLUIDICS, filed Apr. 6, 2020. Each of the foregoing disclosures, in its entirety, is incorporated herein by reference.

BACKGROUND

Surface-binding assays, as exemplified by immunoassay and related techniques, have two essential steps. First, the 'target' (to be measured) is captured onto a surface via a surface-bound 'capture reagent'. The concentration of the target determines the fraction of the capture sites that are 'occupied'. Second, other reagents ('developer' and 'amplifier') are used to determine the amount of target that has been captured, and hence, deduce the target concentration. Classical enzyme-linked immunosorbent assays (ELISA) use an enzyme coupled to an antibody as the 'developer' and 'amplifier'. They are reliable and accurate but are slow to execute and require skilled operators.

The sequence of a classical enzyme-linked immunosorbent assay (ELISA) is as follows:
  prepare a 96-well plate by adsorbing capture reagent (which may be antigen, for a competition or indirect ELISA, or antibody, for a sandwich ELISA),
  prepare a succession of dilutions of the sample to be analysed (called 'titres'), incubate these samples on the plate until equilibrium is attained (at least 1 hour), and wash thoroughly to remove unbound materials, then proceed with the further steps.

Each binding step requires sufficient time to attain equilibrium. The final measurement determines the 'titre' that results in a particular threshold value for the detection signal. Control reagents are used to normalise the results and compensate for variability on the preparation from one plate to another. The whole procedure can take several hours.

To alleviate the problems of time-to-result and the need for a skilled operator, rapid assay tests have been developed, exemplified by pregnancy tests, which give results in a time of 1 to 15 min. In these tests, instead of allowing binding reactions to proceed to equilibrium, they rely on the dependence of the kinetics of binding on the target concentration as a means to relate the assay signal to the target concentration. However, these methods suffer from a lack of precision, giving results which have a typical coefficient of variation of up to 25% together with a significant number of wide outliers (see, for example, "*Point of Care Diagnostics: Status and Future*", Vladimir Gubala, Leanne F. Harris, Antonio J. Ricco, Ming X. Tan, and David E. Williams (2012) *Anal. Chem.*, 84, pp 487-515 DOI: 10.1021/ac2030199). Accordingly, while such rapid assay test is useful for qualitative measurement, particularly for conditions like early pregnancy where the concentration of target hormone almost doubles from one day to the next, these tests have significant issues when an accurate, quantitative measurement is needed.

While microfluidic systems, including systems utilising centrifugal microfluidics, have been widely proposed as a means for achieving accurate immunoassays, a central problem for such systems is mixing of fluids and the achievement of rapid, uniform contact between solids and surfaces. Many different ideas have been proposed, including those with serpentine channels, herringbone structures and, with respect to centrifugal microfluidics, oscillation of disc motion. However, rapid mixing, on a time scale of one or few seconds, would be needed for a rapid assay system directed at high precision. Furthermore, a practical immunoassay system that is automated, fast and suitable for use by minimally trained operators requires critical reagents to be deposited within the assay device during manufacture. Typically, this involves mixing the reagents with a sugar-based solution and then drying this mixture within the assay device. Steps in the assay therefore require that such dried mixtures be resuspended into solution and any soluble reagents dissolved. Speed of mixing and resuspension becomes a critical element if timing is important. In assay systems involving microfluidics such rapid resuspension and re-dissolution has not been achieved.

Thus, it is seen that speed of mixing and precision of timing are essential to achieve precision in any assay system where the determination of concentration is achieved, directly or indirectly, by measurement of reaction rate. In a system that is to be used by minimally-trained operators, where the intervention by the operator is to be limited to changing a simple consumable assay device and applying the sample (whole blood, for example) mixing speed, timing precision and precision in the area of the capture surface and in the fraction of the surface that is occupied by capture reagent must be achieved through manufacture of consumables and automation of assay operation.

SUMMARY OF THE EMBODIMENTS

Embodiments of the present disclosure address the problem of speed to precise result in an immunoassay. Specifically, in the context of the measurement of a biomedical signal species in a situation where a large number of samples (from individuals) need to be processed in an orderly and rapid fashion (for example, at an airport arrival gate or at any other such controlled entry gate) where a decision on access or quarantine needs to be made in a timely and objective fashion.

Disc Based Assays

Accordingly, some of the embodiments of the present disclosure are directed to disc-based immunoassays. Specifically, an immunoassay disc-based measurement system is provided and is configured to process a plurality of samples simultaneously, giving a precise measurement result with short total assay time, can include a centrifugal, microfluidic system configured to at least one of provide different steady rotational speeds with controlled acceleration between speeds, and oscillatory changing direction of rotation with control of acceleration. Thus, ultimate rotation speed controls accurately the motion of the fluids within the disc including mixing, resuspension and dissolution of solids, and timed transfer between chambers.

Such embodiments can also include an assay consumable comprising a multi-layer disc device having fluidic channels, valves, and chambers, a grouping of such configured to process a sample (and each grouping can be referred to as an "assay device"). A plurality of such assay devices can be spaced along a periphery of the disc (e.g., at a particular distance from the center of the disc). Reactive chambers of such assay devices can be configured with a shape and arrangement on the disc so as to ensure speed of mixing and precision of timing of movement of fluids from one chamber to another. Each chamber can include a shape which, in conjunction with motion of a bead, is configured to at least one of induce rapid and uniform mixing of fluids, and rapid and uniform contact of solutions with the surface of a bead. Such functionality can allow the bead to be held by slow rotary motion in a position such that a light beam can pass unimpeded through the chamber.

Assay devices according to some embodiments can also include (some of which briefly mentioned above):
- one or more syphons included and positioned so as to minimise the dead volume and allow timing in the device;
- one or more valves (which can be joined with a siphon or other microfluidic channel), for enabling fluid transitions between components (e.g., components of assay devices), and/or layers of the disc, and can be gated according to a rotational speed of the disc (or an acceleration or deceleration thereof), e.g., enabling fluid migration within small (e.g., capillary) gaps at edges of microchannels. Such valves can also include one or more surface modifications of a contact angle at the entrance of the valve to prevent fluid bridging the valve in an uncontrolled fashion;
- at least one bead of between about 100 μm-2500 μm in diameter (and ranges therebetween) which can be configured to carry a capture reagent, and in some embodiments, the amount of surface coverage of the bead by the capture agent is known. Motion of the bead within a chamber, via motion of the disc, is configured to induce rapid and uniform mixing of the contents therein;
- beads can be made of any material including, for example, polystyrene, polycarbonate, metal-based bead, such as magnetic beads, and the like; any material that allows for chemical conjugation or adsorption of a binding reagents (e.g., antigen, capturing antibody, and the like);
- a mesh material placed within one of the chambers of the assay device (which can be a circular disc of stainless steel mesh of diameter (1-6 mm, and all ranges therebetween) and can include a mesh size of between 10-200 um, and all ranged therebetween), which can be configured to support a dried reagent (e.g., one mixed with sugar), the motion of which via motion of the disc results in rapid re-dispersion and uniform dissolution of the reagent;
- the stainless steel may be type 316 or 306;
- the mesh provides high relative surface area compared to flat surfaces;
- an inlet area for a chamber which enable touchless sample and liquid reagents additions into an assay device, and centrifugal force can be used to displace fluid received the inlet area to a corresponding chamber of the assay device;
- materials of construction can be, e.g., thermoplastics, including poly(methylmethacrylate), polycarbonate, polystyrene or cyclic polyolefin such as Zeonor and the like, with or without the use of pressure sensitive adhesives (PSA), depending on the bonding strategy used, as well as surface treatments (e.g., hydrophobic solution, solvent application and drying, surface roughening, provision of micropillars or pits, application and drying of solution or dispersion of detergents, or of lipids or of poly(tetrafluoroethylene) or other fluorinated polymer or co-polymer, of specific areas, for example, to avoid or decrease the capillary force) can be used and configured to balance effects of capillary forces and hydrodynamic forces, so that fluids flow into certain areas (e.g., a syphon) when desired or required, and that a valve reliably remains closed or opens, during rotation/acceleration, or oscillations (e.g., change in rotational direction) of the disc (e.g., reliably opens upon a transition to higher rotational velocity).

Accordingly, in some embodiments, an assay device is provided, which is configured for arrangement on a disc, as well as configured to process an individual sample. A plurality of such assay devices can be arranged along a periphery of the disc at a distance/radius from the center. Generally, the disc can be any size. As centrifugal force=$w^2 \ast r$, balance thereof can be accomplished via a change in angular speed of the disc, or a distance of an assay device(s) from the center of the disc (in some embodiments, between 10-90% of the radius of the disc, and ranges therebetween). Accordingly, the farther from center, the less angular speed is required to generate a centrifugal force (e.g., to move/flow/transfer/mix fluids/materials). To this end, a plurality of individual samples can be processed, e.g., one per assay device. In addition, in an arrangement that a plurality of assay devices are used, they can be spaced apart such that they balance the disc during rotation (which can be with samples contained in one or more of the assay devices, a plurality, a majority, or all of the assay devices).

The (each) assay device can includes a plurality of chambers (which can be referred to as peripheral chambers) each configured to receive one or more fluids via a respective inlet area, a resuspension chamber including a scaffold for at least one of drying and retaining at least one reagent, and a main chamber having at least one bead therein.

Such assay devices can include one or more of (as well as a plurality of, a majority of, or in some cases, all of) the following advantages, objectives, features, functionality, structure, components, devices, systems, steps, and methods, leading to yet further embodiments of the disclosure:
- the plurality of chambers comprise at least one of a first peripheral chamber, a second peripheral chamber, and a third peripheral chamber;
- the plurality of chambers comprise at least two of a first peripheral chamber, a second peripheral chamber, and a third peripheral chamber;
- the plurality of chambers comprise a first peripheral chamber, a second peripheral chamber, and a third peripheral chamber;
- each peripheral chamber includes a corresponding inlet area;
    - where each inlet area can be configured to flow or otherwise transfer a fluid to a respective peripheral chamber via a siphon or other microfluidic channel;
- the plurality of peripheral chambers includes:
    - a first peripheral chamber having an associated first inlet area, the first inlet area in fluid communication with the first peripheral chamber via a first microchannel, where fluid received in the first inlet area flows into the first peripheral chamber;

a second peripheral chamber having an associated second inlet area, the second inlet area in fluid communication with the second peripheral chamber via a second microchannel, where fluid received in the second inlet area flows into the second peripheral chamber; and/or a third peripheral chamber having an associated third inlet area, the third inlet area in fluid communication with the third peripheral chamber via a third microchannel, where fluid received in the third inlet area flows into the third peripheral chamber;

the resuspension chamber is in fluid communication with a/the second peripheral chamber via an associated microfluidic channel;

a scaffold material comprising a mesh;

the mesh configured as a circular disc, where the disc can be between 1-6 mm (as well as ranges therebetween, including for example, 1-2 mm, 1-3 mm, 1-4 mm, 1-5 mm, 2-3 mm, 2-4 mm, 2-5 mm, 2-6 mm, 3-4 mm, 3-5 mm, 3-5 mm, 4-5 mm, 4-6 mm, and 5-6 mm), or other geometric shape, where the mesh can include a mesh or pore size selected from the group consisting of between: 10-250 μm, between 10-20 μm, between 20-40 μm, 40-60 μm, 60-80 μm, 80-100 μm, 100-120 μm, 120-140, 140-160, 160-180, 180-200, 200-220, 220-240, 240-250, and ranges therebetween;

the main chamber includes a mixing area/chamber arranged distally to the main chamber towards an edge of the disc, where the mixing chamber can include one or more pre-stored reagents;

the main chamber is configured to receive fluid from one or more chambers via associated microfluidic channels (in some embodiments/instances, all);

a mixing area/chamber of the main chamber is configured as a detection window and/or to stabilize the bead during measurements;

the bead includes at least one capture reagent establishing a plurality of binding sites thereon;

the capture reagent of the bead comprises at least one of one or more antibodies and antigens;

the reagent covers a predetermined surface area of a/the at least one bead;

the at least one bead includes a diameter of between 100 μm-2500 μm, and ranges therebetween;

at least one siphon channel;

at least one (e.g., first) siphon channel, which preferably includes associated valve (e.g., microfluidic capillary valve), which is configured to at least one of time and mix a dried reagent for resuspension of the dried reagent in the resuspension chamber;

a/the siphon channel including at least one microfluidic capillary valve being in fluid communication with the resuspension chamber and the main chamber;

a microfluidic pressure release capillary valve in communication with at least one chamber (e.g., the main chamber);

a/the pressure release capillary valve configured to receive the at least one bead after closing of the device;

another/second siphon channel, and associated valve (e.g., microfluidic capillary valve), configured to provide at least one of a timing and mixing in the main chamber;

a waste chamber;

a waste chamber in communication with the main chamber via at least one siphon;

a pressure release outlet in fluid communication with the waste chamber via a microfluid channel;

a/the disc comprises multilayers;

each valve (e.g., microfluidic capillary valve) comprises a capillary gap between layers of the disc;

each valve (e.g., microfluidic capillary valve) comprises a capillary gap between layers of the disc, and is arranged perpendicular to an associated channel;

each valve/capillary valve includes a dried hydrophobic solution configured to decrease wettability at a specific area, such that fluid flow/transitions via the capillary valve is based on a rotational speed of the disc (and/or acceleration/deceleration thereof);

each valve/capillary valve includes at least one of a surface modification of a contact angle at an entrance thereof so as to prevent fluid uncontrolled bridging of the capillary valve, and an increase in pressure to open the valve;

the disc is configured to be spun via a centrifugal microfluidic system, which can include, for example, a programmable motor (e.g., VLM21C-BKNR-30, Kollmorgen with servo drive AKD-P00306-NBAN, Kollmorgen), and imaging/camera system (for example, acA2000-165uc, resolution 2048×1088, 165 fps, coloured—Basler Ace), and/or laser diode/photodiode optical density reading system.

the disc is configured to be spun via a centrifugal microfluidic system which is configured to provide at least one of, and preferably, a plurality of: plurality of different rotational speeds, spin direction, controlled acceleration between speeds, and oscillatory direction of rotation changes, such that, with control of acceleration and rotation, the motion of the fluids within each assay device of the disc including mixing, resuspension and dissolution of solids, and timed transfer between chambers is controlled;

fluid and/or material flow, transfer of fluid and/or materials, pressure increases or decreases, or mixing of a fluid(s) and/or material(s), within an area or a chamber, or among or between two or more areas or chambers, can be accomplished via at least one of rotation of the disc, acceleration and/or deceleration of the disc, and one or more changes in rotational direction of the disc;

rotation, acceleration/deceleration of the disc is according to one or more properties of at least one of a specific fluid, or a specific material, being moved, flowed or otherwise transferred between components or areas of the assay device where rotation of the disc can be at a speed in revolutions-per-minute (RPM) consisting of between: 50-75, 50-100, 50-200, 50-300, 50-400, 50-500, 50-600, 50-700, 50-800, 50-900, 50-1000, 50-1500, 50-2000, 50-2500, 50-3000, 50-3500, 50-4000, or ranges therebetween;

a speed of the rotation of the disc to effect movement of fluid between components is according to a radial location of at least one of the components;

a speed of the rotation of the disc to effect movement of fluid between components is according a volume of the fluid contained in at least one of the components;

two or more chambers are open to one another;

two or more chambers include a partial wall therebetween;

two or more chambers include a partial wall therebetween, and the partial wall is dimensioned such that a first volume of a first chamber is configured to contain a droplet volume less than the first volume, and a second volume of a second chamber is greater than the first volume;

a partial wall is sized such that a gap is established between the two or more chambers; and a partial wall between chambers which is configured to retain a fluid or material therein unless and until acted upon by a centripetal force when the disc is rotated;

Accordingly, in some embodiments, an assay device is provided, which is configured for arrangement on a disc, as well as configured to process an individual sample. A plurality of such assay devices can be arranged along a periphery of the disc at a distance/radius from the center (e.g., between 10-90%, and ranges therebetween), such that a plurality of individual samples can be processed, e.g., one per assay device. In addition, in an arrangement that a plurality of assay devices are used, they can be spaced apart such that they balance the disc during rotation (which can be with samples contained in one or more of the assay devices, a plurality, a majority, or all of the assay devices). Such embodiments have a plurality of peripheral chambers including a first peripheral chamber having an associated first inlet area, the first inlet area in fluid communication with the first peripheral chamber via a first microchannel, a second peripheral chamber having an associated second inlet area, the second inlet area in fluid communication with the second peripheral chamber via a second microchannel, and/or a third peripheral chamber having an associated third inlet area, the third inlet area in fluid communication with the third peripheral chamber via a third microchannel. The device can also include a resuspension chamber including a mesh, the mesh configured as a scaffold for at least one of drying and retaining at least one reagent, where the resuspension chamber is in fluid communication with the second chamber via an associated microfluidic channel, and a main chamber having at least one bead therein. The main chamber can include a mixing area (which can be arranged distally to the main chamber and towards edge of the disc), and can include one or more pre-stored reagents. The main chamber can be configured to receive fluid from at least one of the first, second, and third peripheral chambers via associated microfluidic channels, and the mixing chamber is configured as or to contain, at least one of a detection window, as well as an area to stabilize the bead during measurements. The (at least one) bead includes at least one capture reagent establishing a plurality of binding sites, where the capture reagent comprises at least one of one or more antibodies and antigens over the surface of the at least one bead, the at least beach including a diameter of between 100 μm-2500 μm. The device further includes a first siphon channel configured to time and mix a dried reagent for resuspension for the resuspension of the dried reagent in the resuspension chamber, the siphon including at least one microfluidic capillary valve and being in fluid communication with the resuspension chamber and the main chamber, a microfluidic pressure release capillary valve in communication with the main chamber, and is configured to receive the at least one bead after closing of the device, a second siphon channel configured to provide a timing and mixing in the main chamber, the second siphon include at least one microfluidic capillary valve, a waste chamber in communication with the main chamber via the second siphon, and a pressure release outlet in fluid communication with the waste chamber via a microfluid channel. Fluid and/or material flow, transfer of fluid and/or materials, pressure increases or decreases, or mixing of a fluid(s) and/or material(s), within an area or a chamber, or among or between two or more areas or chambers, is accomplished via at least one of rotation of the disc, acceleration and/or deceleration, and one or more changes in rotational direction of the disc.

In such embodiments, each microfluidic capillary valve can comprise a capillary gap between layers and arranged perpendicular to associated channel and includes a dried hydrophobic solution configured to decrease the wettability of a material at a specific area, such that fluid transitions via the capillary valve is based on a rotational speed of the disc, and a surface modification of a contact angle at an entrance of a respective capillary valve, so as to prevent fluid uncontrolled bridging of the capillary valve.

The disc is configured to be spun via a centrifugal microfluidic system which provides a plurality of different rotational speeds, different spin directions, controlled acceleration and/or deceleration between speeds, and oscillatory direction of rotation changes, such that, with control of acceleration and ultimate rotation speed controls accurately the motion of the fluids within the disc including mixing, resuspension and dissolution of solids, and timed transfer between chambers is accurately controlled.

Such assay devices can include one or more of (as well as a plurality of, a majority of, or in some cases, all of) the following advantages, objectives, features, functionality, structure, components, devices, systems, steps, and methods, leading to yet further embodiments of the disclosure:

rotation, acceleration/deceleration of the disc is according to one or more properties of at least one of a specific fluid, or a specific material, being moved, flowed or otherwise transferred between components or areas of the assay device;

rotation of the disc can be at a speeds in revolutions-per-minute (RPM), and/or at accelerations of RPM/s, consisting of between: 50-75, 50-100, 50-200, 50-300, 50-400, 50-500, 50-600, 50-700, 50-800, 50-900, 50-1000, 50-1500, 50-2000, 50-2500, 50-3000, 50-3500, 50-4000, 500-1000, 500-2000, 500-3000, 500-4000, 1000-2000, 1000-3000, 1000-4000, 2000-3000, 2000-4000, or ranges therebetween;

the speed of the rotation of the disc to effect movement of fluid between components is according to a radial location of at least one of the components;

the speed of the rotation of the disc to effect movement of fluid between components is according a volume of the fluid contained in at least one of the components;

two or more chambers are open to one another, and can include a partial wall therebetween, such that, the partial wall can be dimensioned such that a first volume of a first chamber is configured to contain a droplet volume less than the first volume, and a second volume of a second chamber is greater than the first volume;

a partial wall between chambers sized such that a gap is established between the two or more chambers, and a partial wall between chambers configured to retain a fluid or material therein unless and until acted upon by a centripetal force when the disc is rotated;

The present disclosure also includes embodiments for an immunoassay disc device configured for processing a plurality of samples simultaneously, which includes a plurality of assay devices according to any assay devices disclosed herein (e.g., see above).

The present disclosure also includes embodiments for an immunoassay system comprising an immunoassay disc device configured for processing a plurality of samples simultaneously, which includes a plurality of assay devices according to any assay devices disclosed herein (e.g., see above), and a centrifuge system for spinning the disc.

In some embodiments, a centrifugal assay method for performing an assay on a sample via an immunoassay device contained on a disc, is provided and includes receiving of a sample by a peripheral chamber of an assay device of an assay disc, and transferring the sample to a mixing area of a main chamber of the assay device, the mixing chamber including at least one functionalized bead therein.

Such methods can include one or more of (as well as a plurality of, a majority of, or in some cases, all of) the following advantages, objectives, features, functionality, structure, components, devices, systems, steps, and methods, leading to yet further embodiments of the disclosure:
  receiving a first washing solution by the assay device;
  the first washing solution is received by the peripheral chamber;
  flushing the sample from the mixing area of the main chamber to a waste chamber of the assay device;
  receiving a resuspension by the assay device;
  a resuspension solution is received in a second peripheral chamber of the assay device;
  flowing, or otherwise transferring, and optionally holding a/the resuspension solution in a resuspension chamber of the assay device so as to resuspend dried reagent stored therein;
  transferring a/the resuspended reagent from a/the resuspension chamber to the mixing area/chamber of the main chamber;
  mixing a/the resuspended reagent with the at least one bead;
  receiving a second washing solution by the assay device;
  transferring a/the second washing solution to the peripheral chamber;
  transferring a/the second washing solution to a/the peripheral chamber, and/or the main chamber;
  flushing a/the resuspended reagent solution from the mixing area of the main chamber to a/the waste chamber;
  receiving a colorimetric solution, such as, e.g., 3,3',5,5'-Tetramethylbenzidine (TMB) Liquid Substrate System for ELISA, 2,2'-Azino-bis(3-ethylbenzothiazoline-6-sulfonic acid, diammonium salt, (ABTS), OPD Substrate tables (o-phenylenediamine dihydrochloride), by the assay device, Sigma-Aldrich product T4444, CAS Number 54827-17-7, and the like;
  receiving and/or transferring a/the colorimetric solution to a peripheral chamber of the assay device;
  transferring a/the colorimetric solution from a/the peripheral chamber to the mixing area of the main chamber, such that the colorimetric solution mixes with the at least one bead;
  kinetically and/or statically measuring a colorimetric signal produced by the assay device, where the signal is produced during mixing (or thereafter);
  receiving of one or more fluids or material, including a sample, is via an inlet area for a respective chamber, where at least one fluid can be transferred to from an inlet area to a respective chamber;
  at least one of fluid and/or material flow, transfer of fluid and/or materials, pressure increases or decreases, or mixing of a fluid(s) and/or material(s), within an area or a chamber, or among or between two or more areas or chambers, is accomplished via at least one of rotation of the disc, acceleration and/or deceleration of the disc, and one or more changes in rotational direction of the disc;
  rotation, acceleration/deceleration of the disc can be according to one or more properties of at least one of a specific fluid, or a specific material, being moved, flowed or otherwise transferred between components or areas of the assay device;
  rotation of the disc is at a speed in revolutions-per-minute (RPM), and/or accelerations of RPM/s, consisting of between: 50-75, 50-100, 50-200, 50-300, 50-400, 50-500, 50-600, 50-700, 50-800, 50-900, 50-1000, 50-1500, 50-2000, 50-2500, 50-3000, 50-3500, 50-4000, 500-1000, 500-2000, 500-3000, 500-4000, 1000-2000, 1000-3000, 1000-4000, 2000-3000, 2000-4000, or ranges therebetween;
  the speed of the rotation of the disc to effect movement of fluid between components is according to a radial location of at least one of the components; and
  the speed of the rotation of the disc to effect movement of fluid between components is according a volume of the fluid contained in at least one of the components.

In some embodiments, a centrifugal assay method for performing an assay on at least one sample via an immunoassay device, is provided and includes placing a sample in a first inlet area of an assay device of an assay disc, the inlet area configured to hold the sample therein, transferring the sample to a first peripheral chamber of the assay device, transferring the sample from the first peripheral chamber to a mixing area of a main chamber of the assay device via a second syphon and associated capillary valve of the assay device, placing a first washing solution in the first inlet area, transferring the washing solution to the first peripheral chamber, then to the main chamber, opening a capillary valve associated with a siphon for fluid communication between the mixing area of the main chamber and a waste chamber of the assay device, such that the sample is flushed from the mixing area of the main chamber to the waste chamber, placing a resuspension solution in a second inlet area of the assay device, transferring the resuspension solution from the second inlet area to a second peripheral chamber of the assay device, transferring and holding the resuspension solution in a resuspension chamber of the assay device so as to resuspend dried reagent from a wire mesh therein, transferring the resuspended reagent from the resuspension chamber to the main chamber via the opening of a capillary valve associated with the siphon of the assay device associated with fluid communication between the mixing area of the main chamber and the resuspension chamber, such that the mixing area of the main chamber receives the resuspended reagent from the resuspension chamber and the resuspended reagent is mixed with the at least one bead, placing a second washing solution in the first inlet area, transferring the second washing solution to the first peripheral chamber, then to the main chamber, flushing the resuspended reagent solution from the mixing area of the main chamber to the waste chamber via the opening of the capillary valve associated with the second siphon, placing a colorimetric solution in a third inlet area of the assay device, transferring the colorimetric solution to a third peripheral chamber of the assay device, then to the mixing area of the main chamber, such that the colorimetric solution mixes with the at least one bead via rotation of the disc, and kinetically or statically measuring a colorimetric signal during mixing, spin or resting period.

Such methods can include one or more of (as well as a plurality of, a majority of, or in some cases, all of) the following advantages, objectives, features, functionality, structure, components, devices, systems, steps, and methods, leading to yet further embodiments of the disclosure:
  the method is performed on a plurality of samples via a plurality of assay devices each arranged on the disc along a periphery thereof at a predetermined radius in a spaced apart arrangement;

rotation, acceleration/deceleration of the disc is according to one or more properties of at least one of a specific fluid, or a specific material, being moved, flowed or otherwise transferred between components or areas of the assay device;

rotation of the disc is at a speed in revolutions-per-minute (RPM), and/or accelerations of RPM/s, consisting of between: 50-75, 50-100, 50-200, 50-300, 50-400, 50-500, 50-600, 50-700, 50-800, 50-900, 50-1000, 50-1500, 50-2000, 50-2500, 50-3000, 50-3500, 50-4000, 500-1000, 500-2000, 500-3000, 500-4000, 1000-2000, 1000-3000, 1000-4000, 2000-3000, 2000-4000, or ranges therebetween;

the speed of the rotation of the disc to effect movement of fluid between components is according to a radial location of at least one of the components;

the speed of the rotation of the disc to effect movement of fluid between components is according a volume of the fluid contained in at least one of the components; and fluid and/or material flow, transfer of fluid and/or materials, pressure increases or decreases, or mixing of a fluid(s) and/or material(s), within an area or a chamber, or among or between two or more areas or chambers, is accomplished via at least one of rotation of the disc, acceleration and/or deceleration, in some embodiments, between 200-3000 rpm/s (including any ranges therebetween: e.g., 200-300, 200-500, 200-1000, 200-1500, 200-2000, 200-3000, 500-1000, 500-2000, 500-3000, 1000-2000, 1000-3000); and one or more changes in rotational direction of the disc (e.g., in some embodiments between 50 and 200 times and ranges therebetween, e.g., 50-100, 50-150, 100-150, 100-200, 150-200).

With respect to changes in direction, and in particular, mixing, a total mixing cycle can be between, e.g., 50 to 100 seconds (and ranges therebetween, e.g., 50-75, 75-100), with each individual cycle being between 0.1 to 10 seconds, and any ranges therebetween (e.g., in seconds, 0.1-1, 0.1-2, 0.1-3, 0.1-4, 0.1-5, 0.1-6, 0.1-7, 0.1-8, 0.1-9, 0.1-0.5, 2-3, 2-4, 2-5, 2-5, 2-7, 2-8, 2-9, 2-10, and the like); specifically, the disc is rotating in one direction until it reaches at least one of a set speed and acceleration, the disc can then be stopped (e.g., between about 1-100 ms), and then rotated in the opposite direction. This process can be repeated a number of times (in some embodiments, between 50-200 times). As noted above, in some embodiments, mixing need not be via a change in direction, but rather, via acceleration or deceleration, moreover, the disc can be rotated in one direction for a period of time, the disc can be stopped, then accelerated in the same direction.

Vial-Based Assays

In some embodiments of the disclosure, a vial-based assay system and/or kit is provided which includes a first reaction vial, having a first size, shape, and volume of between 0.01-150 ml (and ranges therebetween, e.g., 0.01-10 ml, 0.01-25 ml, 0.01-50 ml, 0.01-75 ml, 0.01-100 ml, 0.01-125 ml), including at least one functionalized bead of between 10 µm to 5000 µm (and ranges therebetween, e.g., 10-100, 10-250, 10-500, 10-1000, 10-2500, 10-3000, 10-4000, 10-5000, 100-500, 100-1000, 100-2500, 1000-3000, 100-4000, 100-5000, 500-1000, 500-2500, 500-3000, 500-4000, 500-5000, 1000-2000, 1000-3000, 1000-4000, 1000-5000, 2500-5000) in diameter, the at least one bead including a plurality of binding sites for at least on antigen and a dried or liquid conjugate of the at least one antigen, the first vial optionally including a dried detergent comprising at least one of Tween, Brij, and pluronic. The system or kit can also include a second, washing/filter vial, having a second size, shape, and volume of between 0.01-150 ml (and ranges therebetween—see above), including a barrier, which can comprise a filter, having a size, or a pore size, smaller than a size of the at least one bead so as to hold the at least one bead during washing step. Optionally, a third, waste vial, can be included, which may have a third size, shape, and volume, configured for receiving waste. The system or kit can further include a fourth vial, having a fourth size, shape, and volume, including a colorimetric reagent and buffer powder containing a reactant to support an enzymatic colorimetric assay. Optionally, the system or kit can include a fifth vial, having a fifth size, shape, and volume.

In some embodiments, an assay method is provided (which uses the system/kit according to disclosed embodiments, such as detailed above), which includes (a) adding a sample containing a target comprising at least one of an antigen, molecule, and protein for quantification, to a first vial containing at least one functionalized bead of between 10 µm to 5000 µm in diameter (and ranges therebetween, see e.g., above), the at least one bead including a plurality of binding sites comprising at least one first antigen and a dried or liquid conjugate of the at least one first antigen, the first vial optionally including a dried detergent comprising at least one of Tween, Brij, and pluronic. The method further includes (b) mixing the sample within the first vial for a predetermined period of time, whereby the antigen and antigen-conjugate compete for binding sites on the bead, (c) removing the sample from the vial, and (d) transferring the at least one bead from the first vial to a second vial having a barrier component comprising a filter. The transfer can be accomplished via a connection of the first vial to the second vial. For a washing procedure, the method can include configuring the first vial as a waste chamber, or disconnecting the first vial from the second vial and connecting a third vial configured to act as the waste chamber, where transfer of fluid from the second vial to the waste chamber is performed either via gravity and/or via application of pressure. The method also includes (e) washing the bead at least once, washing comprising adding an aqueous buffer solution (which can comprise a saline buffer, which can include tween) to the second vial $b_0$, centrifuging the compound (attached) vials for an amount of time to wash the bead, and discarding the aqueous solution from the second vial into the waste chamber, where the washed bead includes captured antigens and antigen-conjugates, and excess antigen has been washed off. In some embodiments, ready to use buffer solution can be supplied (e.g., via the system or kit, and/or via the method), and/or water can be added to a dried buffer pellet to resuspend it to make the buffer). The method may further include (f) transferring the at least one bead from the second vial to fourth vial, (g) adding a predetermined amount of purified water (e.g., a colorimetric solution, e.g., 3,3',5,5'-Tetramethylbenzidine (TMB) Liquid Substrate System for ELISA, OPD Substrate Tablets (o-phenylenediamine dihydrochloride), 2,2'-Azino-bis(3-ethylbenzothiazoline-6-sulfonic acid) diammonium salt, (ABTS)), to the fourth vial, such that, a colorimetric reaction occurs, (h) reading out a signal from the fourth vial of the colorimetric solution via a reader, and (i) optionally stopping the colorimetric solution via addition of an acid solution to the fourth vial. Ready to use colorimetric solutions (e.g., TMB), can be provided, and/or one or more pellets to resuspend to form a colorimetric solution (which can be encapsulated (which are water soluble, e.g., gelatin, sugar) so as to prevent being reactive among a plurality thereof). Usually some of the pellets to make the drying solution may be reactive if touch each other. Colorimetric reagents can include, e.g., 3,3',5, 5'-Tetramethylbenzidine (TMB) Liquid Substrate System for ELISA (brand names, e.g., ABCAM, Sigma Aldrich), OPD Substrate Tablets (o-phenylenediamine dihydrochloride), and 2,2'-Azino-bis(3-ethylbenzothiazoline-6-sulfonic acid) diammonium salt, (ABTS);

Such methods can include one or more of (as well as a plurality of, a majority of, or in some cases, all of) the following advantages, objectives, features, functionality, structure, components, devices, systems, steps, and methods, leading to yet further embodiments of the disclosure:
    the at least one bead includes a second plurality of binding sites comprising a second antigen;
    the at least one bead includes a second plurality of binding sites comprising a second antigen, and wherein method further comprises, before step (f), performing a step of adding a defined amount of purified water to the fourth vial, and thereafter, allowing the captured target to bind with the second antigen; and
    repeating step (e) at least once.

Accordingly, these and other features, objects, and advantages of embodiments of the disclosure will become even more evident by the following detailed description (of some of the embodiments), and corresponding figures associated therewith, a brief description of which is provided below.

BRIEF DESCRIPTION OF THE DRAWINGS

FIG. 4 is a chart illustrating rotational speeds/accelerations, of a disc having thereon one or more assay devices (e.g., FIGS. 1-2), for achieving at least one of fluid/material movement among components of the assay device, and/or mixing thereof, according to some embodiments;

FIGS. 5A-B illustrate a sectional view of an inlet area and an associated chamber of an assay device, according to some embodiments of the disclosure;

FIG. 6 is a schematic representation of a main chamber for an assay device according to some embodiments of the disclosure;

DETAILED DESCRIPTION OF SOME OF THE EMBODIMENTS

Disc Based Assay Embodiments

Figure 1:
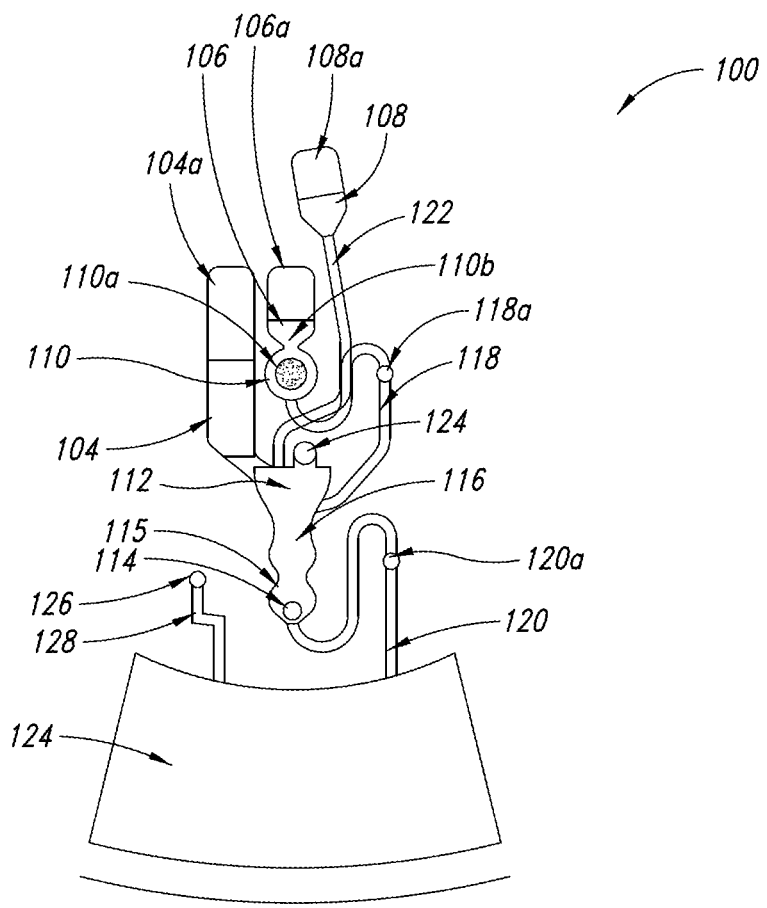
FIG. 1 is a schematic representation of an assay device for a disc based assay system, one or more of which for inclusion on an assay disc, according to some embodiments of the disclosure.
Figure 2:
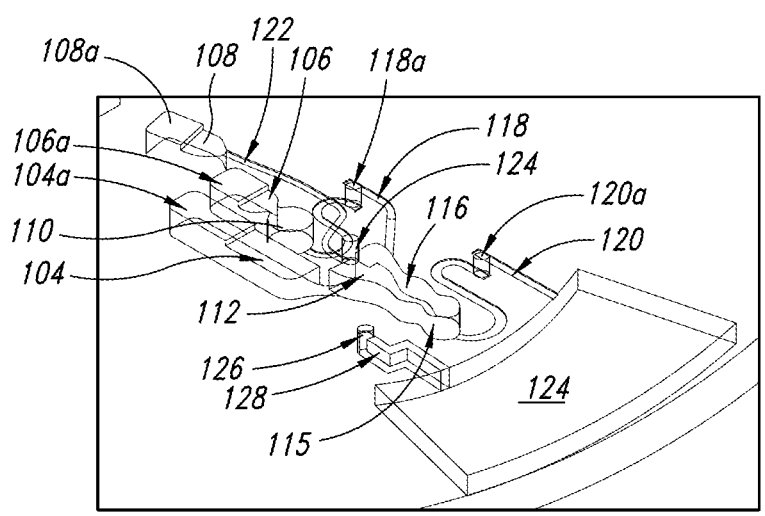
FIG. 2 is a perspective, three-dimensional representation of the assay device of FIG. 1, according to some embodiments of the disclosure.
Figure 10A:
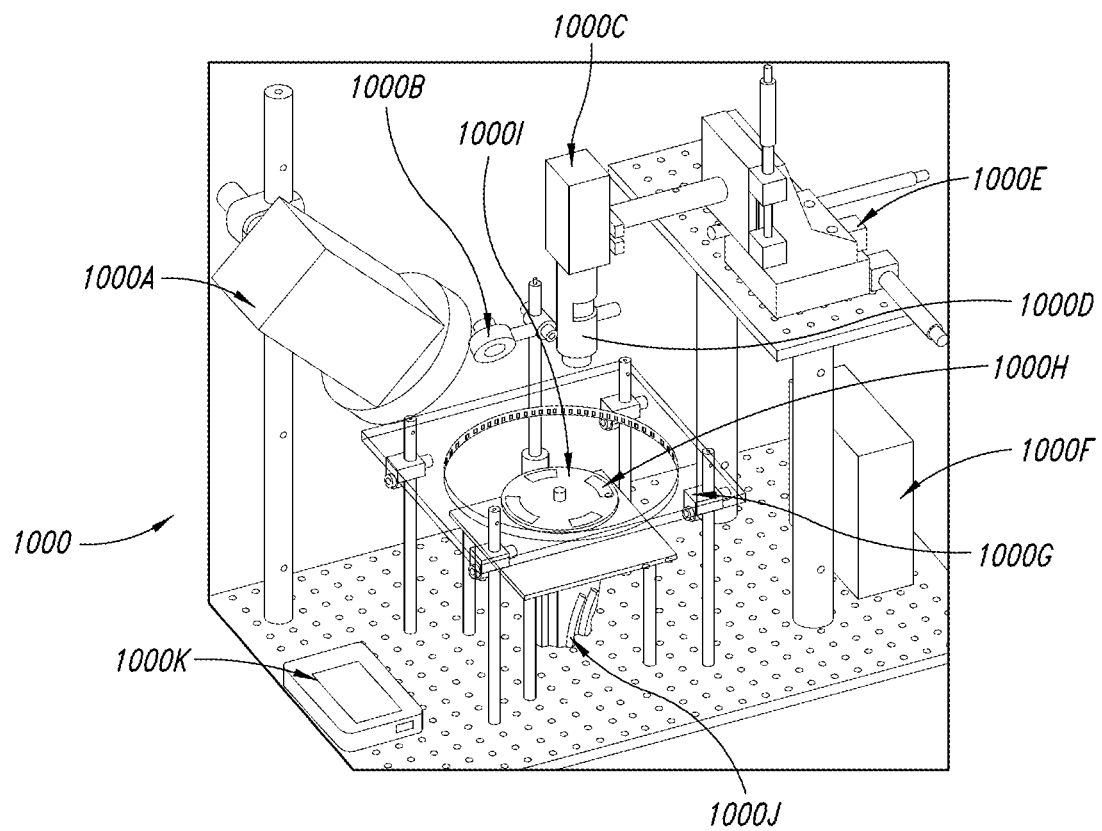
FIGS. 10A-I, are various illustrations of a microfluidic pneumatic centrifuge mixing system/apparatus, including an example use thereof (see FIG. 10I), according to such embodiments of the disclosure.
Figure 10B:
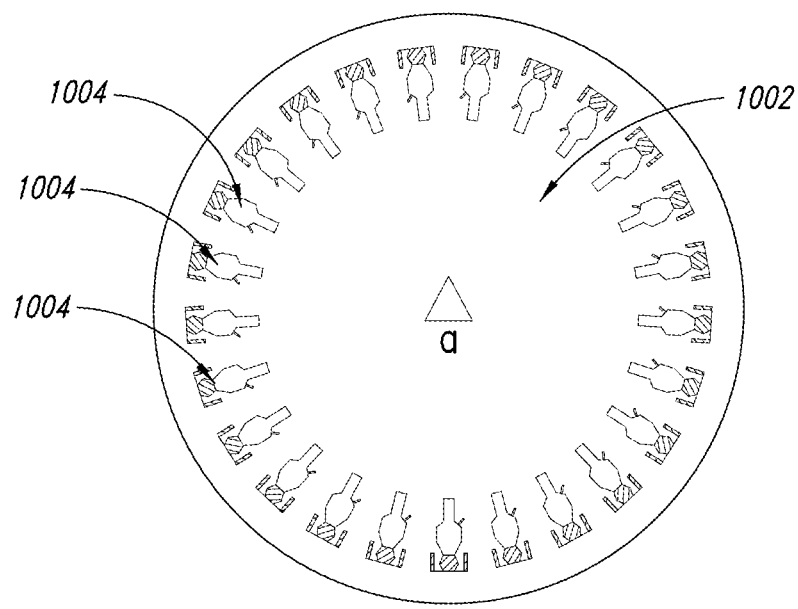

As shown in FIGS. 1-2, an assay device 100 is provided, which is configured for arrangement on a disc device 102 (see also, e.g., FIG. 10A, illustrating a disc device 1002, which can be configured to have thereon, a plurality of assay devices 100). The disc device is configured for rotating on a centrifuge device/system (see, e.g., FIG. 10A) for effecting various fluid flows and missing. Such centrifuge devices/system can be, for example, VLM21C-BKNR-30, Kollmorgen with servo drive AKD-P00306-NBAN, Kollmorgen), and imaging/camera system (for example, acA2000-165uc, resolution 2048×1088, 165 fps, coloured—Basler Ace), and/or laser diode/photodiode optical density reading system.

The assay device 100, according to some embodiments, is configured to process an individual sample (and in some embodiments, a plurality of samples). The assay device 100 (and in some embodiments, a plurality of assay devices, are positioned along a periphery of the disc 102 at a predetermined radius in a spaced apart arrangement. The disc, as well as the assay device(s) thereof, can be multi-layered. Discs can be made of any type material, and preferably, of thermoplastic (e.g., PMMA, Polycarbonate, PLA, PET, and the like), with or without the use of pressure sensitive adhesives (PSA), depending on a bonding strategy used. For example, e.g., acrylic layers bound by pressure sensitive adhesives (PSA), such that an acrylic layer which can include inlet and pressure release valves, channels and chambers cut from PSA, then layer of acrylic.

It is noted that in such embodiments, any flow, transfer or movement of fluid and/or material from one component, chamber, microchannel, siphon, or area to another component, chamber, microchannel, siphon, or area, is via rotation of the disc. Particularly, in some embodiments, such movement is effected by at least one of: accelerating or decelerating the disc, rotating the disc at a set (and which can be steady), starting or stopping the disc, and reversing rotational direction of the disc one or more times. Similarly, mixing a fluid or material (or pressurizing a fluid or material) in one or more areas can be accomplished via at least one of: accelerating or deceleration the disc, rotating the disc at a set (and which can be steady), starting or stopping the disc, and reversing rotational direction of the disc one or more times (which may also be referred to as oscillatory motion of the disc, or oscillations thereof). This can be referred to as, with respect to the disc, as "rotating", "rotated", or "rotation". Accordingly, reference to any fluid/material flow, transfer or mixing is according to the above, unless otherwise indicated (see also, the table of FIG. 4 indicating various acceleration speeds of a disc according to some embodiments, and associated respective tasks—see, e.g., FIGS. 3A-O). This can be referred to as "mixed" or "mixing".

Accordingly, the disc, according to some embodiments, with assay devices arranged or otherwise integrated thereon is configured to be spun via a centrifuge, such that the system provides any or plurality of different rotational speeds, spin direction, controlled acceleration between speeds, and oscillatory direction of rotation changes. Thus, with control of acceleration and rotation, the motion of the fluids within each assay device of the disc including mixing, resuspension and dissolution of solids, can be timed so as to, for example, control transfer between chambers. Moreover, fluid and/or material flow, transfer of fluid and/or materials, pressure increases or decreases, or mixing of a fluid(s) and/or material(s), within an area or a chamber, or among or between two or more areas or chambers, can be accomplished via at least one of rotation of the disc, acceleration and/or deceleration of the disc, and one or more changes in rotational direction of the disc. As previously noted, FIG. 4 shows example rotation speeds/accelerations (in RPM, RMP/s) for various tasks of an assay method (see, e.g., FIGS. 3A-O).

Moreover, rotation, acceleration/deceleration of the disc can be according to one or more properties of at least one of a specific fluid, or a specific material, being moved, flowed or otherwise transferred between components or areas of the assay device. In some embodiments, rotation of the disc can be at a speed in RPM consisting of between: 50-75, 50-100, 50-200, 50-300, 50-400, 50-500, 50-600, 50-700, 50-800, 50-900, 50-1000, 50-1500, 50-2000, 50-2500, 50-3000, 50-3500, 50-4000, or ranges therebetween (see, e.g., other disclosed ranges in this disclosure). Also, a required speed of the rotation of the disc to effect movement of fluid between components of an assay device can be according to a radial location thereof, or of at least one of the components. Additionally, in some embodiments, a speed of the rotation of the disc to effect movement of fluid between components can be according a volume of the fluid contained in at least one of the components.

Accordingly, as shown in the figures, each assay device 100 can include a plurality of chambers, which can be referred to as peripheral chambers, and can include, for example, a first peripheral chamber 104 having an associated first inlet area 104a, where the first inlet area in fluid communication with the first peripheral chamber via a first microchannel or gap 104b (see, e.g., 504, FIGS. 5A-B). Fluid received in the first inlet area can flow into the first peripheral chamber via rotation of the disc A second peripheral chamber 106 can be provided which can include an associated second inlet area 106a, the second inlet area in fluid communication with the second peripheral chamber via, for example, a second microchannel or gap (see, e.g., 504, FIGS. 5A-B). Fluid received in the second inlet area can flow into the second peripheral chamber via rotation of the disc.

The plurality of chambers also can include a third peripheral chamber 108 having an associated third inlet area 108a, the third inlet area in fluid communication with the third peripheral chamber via a third microchannel or gap (see, e.g., 504, FIGS. 5A-B), and fluid received in the third inlet area flows into the third peripheral chamber via rotation of the disc. Placement of fluids or materials in various inlets area is preferably done so that the fluid/material is placed at the base/bottom of an inlet area.

The assay device can also include a resuspension chamber 110 can include a mesh 110a, the mesh configured as a scaffold for at least one of drying and retaining at least one reagent. The resuspension chamber can be in fluid communication with the second chamber via an associated microfluidic channel or opening 110b, and fluid is configured to flow therebetween via rotation of the disc. The resuspension chamber 110 can be immediately adjacent chamber 106, and in combination therewith, can form an hourglass shape. The mesh can comprise a circular disc (or other geometric shape, of between 1-6 mm (and can be any range therebetween), and can be made of stainless steel, which can include a mesh of between 10-200 µm (and any range/size therebetween, see, e.g., disclosed ranges for mesh, supra).

The assay device may include a main chamber 112 having at least one bead 114. The main chamber can include a mixing area/chamber 116 arranged as part of (e.g., distally to the main chamber 112) in a direction towards edge of the disc 102, and can include one or more pre-stored reagents. The main chamber 112 can also be configured to receive fluid from each of the first, second, and/or third peripheral chambers via associated siphons/microfluidic channels (e.g., 118, 120, 122), and the mixing chamber 116 can be configured as a detection window, or include a detection window, as well as an area 115 to stabilize the bead during measurements.

Beads can be made of any material (e.g., polystyrene, polycarbonate, metal-based bead, such as magnetic beads, and the like) that allows for chemical conjugation and/or adsorption of one or more binding reagents (e.g., antigen, capturing antibody, and the like). Accordingly, the at least one bead can include at least one capture reagent, which preferably establishes a plurality of binding sites, and the capture reagent can comprise at least one of one or more antibodies and antigens covering at least a portion of the surface of the at least one bead, and can include a diameter of between 100 µm-2500 µm, and any range therebetween.

The assay device can also include a first siphon channel 118 configured to time and mix a dried reagent for resuspension for the resuspension of the dried reagent in the resuspension chamber 110. The siphon can include at least one microfluidic capillary valve 118a and (in some embodiments) is in fluid communication with the resuspension chamber 110 and the main chamber 112.

In some embodiments, a microfluidic pressure release capillary valve 124 is included, which can be in communication with the main chamber 112, and can be configured to receive the at least one bead 114 after closing of the device, e.g., placing a dry reagent before the device is closes (in preferred embodiments the devices are not opened or closed during runs.

The assay device can also include a second siphon channel 120 configured to provide a timing and mixing in the main chamber, the second siphon 120 can include at least one microfluidic capillary valves 120a. In some embodiments, a waste chamber 124 is included, which can be configured to be in communication with the main chamber via the second siphon. The waste chamber may also include a pressure release outlet 126 which can be in fluid communication with the waste chamber via microfluid channel 128.

Valves of the embodiments of the present disclosure can be microfluidic capillary valves, which can be a capillary gap between layers of disc (see valves 118a, 120a, FIG. 2), and can be arranged perpendicular to an associated siphon/microchannel. Each valve can include a dried hydrophobic solution configured to decrease wettability at a specific area, such that fluid flow/transitions via the valve via rotation, are better able to be performed. Similarly, a valve can include at least one of a surface modification of a contact angle at an entrance thereof, so as to prevent fluid uncontrolled bridging of the capillary valve, and an increase in pressure to open the valve (e.g., in some embodiments, the contact angle is greater than 90 degrees.

In some embodiments of the assay device, two or more chambers are open to one another, and can also include a partial wall therebetween. The partial wall can be dimensioned such that a first volume of a first chamber is configured to contain a droplet volume less than the first volume, and a second volume of a second chamber is greater than the first volume. A partial wall can be sized such that a gap is established between the two or more chambers. Use of a partial wall between chambers can be configured to retain a fluid or material therein, unless and until acted upon by a centripetal force when the disc is rotated. This is shown in FIGS. 5A-B. FIG. 5A illustrates depositing fluid 503 through an opening 502b for an inlet area 502a (the fluid insertion tool can be a pipette, for example). Preferably, the fluid is deposited on the bottom surface/area of the inlet area 502a. The assay device (to which a portion 500 thereof is illustrated), includes structures, partial wall 504, top/first portion/surface 506, and bottom/second portion/surface 508, which can be part of the disc layers, for establishing components of each assay device. The partial wall 504 is configured such that a gap (which can be referred to as a capillary gap or, a microfluidic channel). This gap is configured to contain a fluid in the inlet area 502a, where the fluid contained only moves through the gap through the disc being rotated (resulting in centripetal force "$F_c$" causing movement of fluid/materials from 502a inlet area to chamber 502 via gap 504a).

In some embodiments, a centrifugal assay method for performing an assay on a sample via an immunoassay device contained on a disc is provided. As noted earlier in the disclosure, any flow, transfer or movement of fluid and/or material from one component, chamber, microchannel, siphon, or area to another component, chamber, microchannel, siphon, or area, is via rotation of the disc (See earlier disclosure of rotation).

As shown in FIG. 6, the shape of the main chamber 112 can be configured to optimise cleaning and mixing in mixing area 116, as shown by the arrows. In addition, the mixing area 116 is configured with portion/area 115, sized and/or shaped to contain the at least one bead at rest, such that, in some embodiments, the bead is removed from the mixing area/detection window 116 during measurements (for example).

Figure 7A:
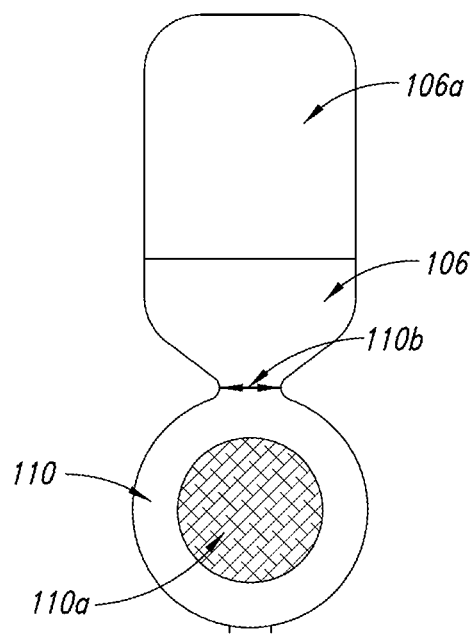
FIG. 7A is a schematic representation of an inlet area, associated chamber, and resuspension chamber, for an assay device according to some embodiments of the disclosure.
Figure 7B:
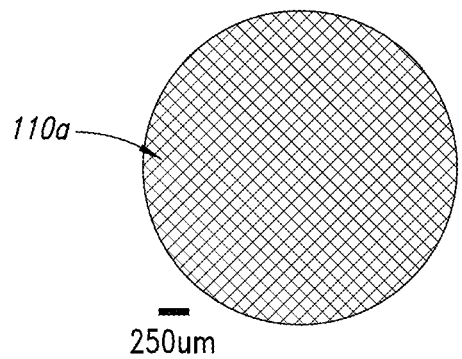
FIG. 7B is a schematic representation of an example of a mesh which is contained or otherwise placed in a resuspension chamber of an assay device, according to some embodiments of the disclosure.

FIG. 7 is an illustration of chamber 106, as well as inlet area 106a, and resuspension chamber 110 containing a mesh 110a, where a gap 110b is established be established to allow fluid to transfer from chamber 106 to resuspension chamber 110.

Figure 3A:
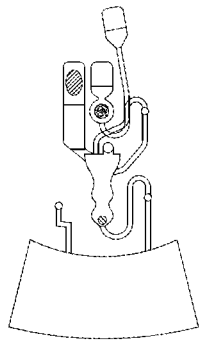
FIGS. 3A-O are depictions of the assay device of FIGS. 1-2, as it is used in a method for performing an assay, according to some embodiments of the disclosure.
Figure 3B:
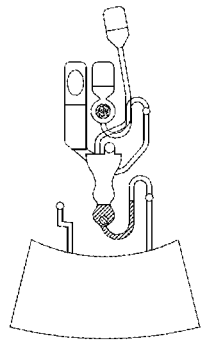
Figure 3C:
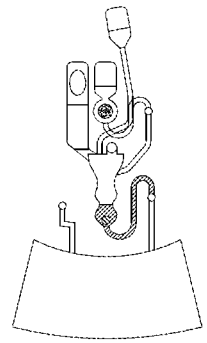

Accordingly, FIGS. 3A-O illustrate a method according to some embodiments (the structure of the assay device shown in FIGS. 3A-O is the same as that which is illustrated in FIGS. 1-2, thus, the same reference numbers correspond to the structures of the assay device shown in FIGS. 3A-O as that in FIGS. 1-2). One and/or another of the steps illustrated in FIGS. 3A-O can be, in some embodiments, repeated (e.g., washing step(s)). Accordingly, the method can include, placing a sample in inlet area 104a (FIG. 3A), which is preferably deposited on the bottom wall of the inlet area, the sample being held their (i.e., via the design thereof). The disc is then accelerated/rotated such that the sample (e.g., blood) is transferred to the first chamber 104 (FIG. 3B), then to main chamber 112, where it can be positioned in the mixing area 116 thereof (and/or within area 115). The sample can then be held in the mixing area 116 (FIG. 3C) (and/or within area 115), via closed valved 120a such that the sample does not proceed to waste chamber via siphon 120. Accordingly, the sample mixes with the at least one bead 128. Mixing (as previously disclosed), can be had via reversing rotational motion a plurality of times and/or subjecting the assay device(s) on the disc to accelerations and decelerations (and/or at steady rotational speeds).

Valves can be opened by, for example, by adding fluid above a siphon and spinning the disk up to a speed, e.g., 3600 RPM, at an acceleration of 1200 RPM/s for example); this valve can be associated with the main chamber (e.g., siphon/valve associated with the main chamber). In some embodiments, a range of disc speeds can be used, including 50-5000 rpm, 50-5000 rpm/s (and any range therebetween for either value), for both speed and acceleration. A valve associated with a reagent chamber (e.g., the resuspension chamber with a mesh) can be opened by a relatively high speed and slower acceleration, e.g., 4000 rpm, 250 rpm/s.

For mixing, and with respect to changes in direction, a mixing cycle can be between, e.g., 50 to 100 seconds; specifically, the disc is rotating in one direction until it reaches at least one of a set speed and acceleration, the disc can then be stopped (e.g., between about 1-100 ms), and then rotated in the opposite direction. This process can be repeated a number of times (in some embodiments, at 50-200 times). As noted above, in some embodiments, mixing need not be via a change in direction, but rather, via acceleration or deceleration, moreover, the disc can be rotated in one direction for a period of time, the disc can be stopped, then accelerated in the same direction.

Figure 3D:
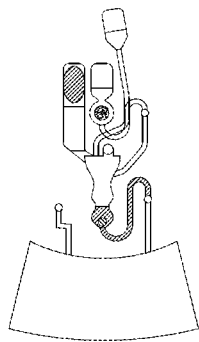
Figure 3E:
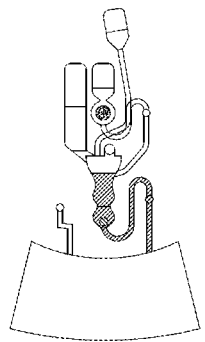

Thereafter, disc rotation stops, and a washing solution is placed in inlet 104a (FIG. 3D), and transfer thereof to chamber 104 (FIG. 3E), then to the main chamber 112 via rotation of the disc (see above, regarding transfer of sample from inlet area to first chamber, then to the main chamber). By opening valve 120a on siphon 120, the sample is flushed from the mixing area/chamber 116 (and/or area 115) of the main chamber 112 and into the waste chamber 124 via siphon 120 (FIG. 3E). Such movement via the siphon is via rotation of the disc. Once the washing solution passes into the waste chamber 124, valve 120a can be closed.

Figure 3F:
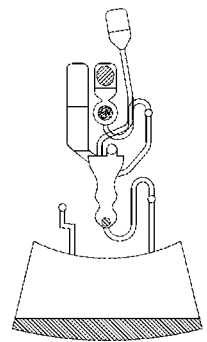
Figure 3G:
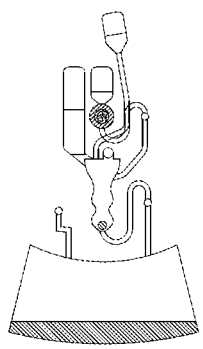
Figure 3H:
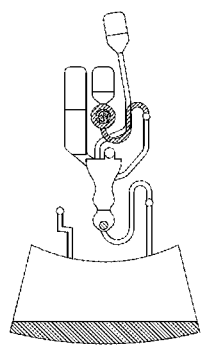
Figure 3I:
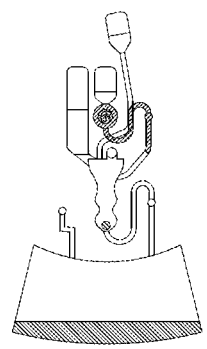

Disc rotation is stopped, and a resuspension fluid is placed in inlet area 106a (FIG. 3F), which is held therein (when the disc is motionless). Upon disc rotation, the resuspension fluid is transferred to chamber 106, and then onto resuspension chamber 110, where it interacts with mesh 110a so as to interact with the mesh having dried reagents provided thereon (FIG. 3G). The resuspension fluid is held within chamber 110 during any rotation of the disc, since valve 118a is closed, and thus, siphon/microchannel 118 cannot operate to move the resuspension fluid to the main chamber 112 (FIG. 3H). Once valve 118a is open, rotation of the disc causes the resuspension fluid to flow into main chamber 112, then onto the mixing area 116 (and/or area 115) containing the at least one bead (FIG. 3I). The resuspension fluid with resuspended reagent is then held within the mixing area 116 when valve 120a is closed (such that siphon 120 cannot transfer fluids to the waste chamber 124) (FIG. 3J), and can be mixed.

Washing solution received by inlet area 104a (FIG. 3K) can then be transferred chamber 104, then onto main chamber 112 via rotation of the disc. Valve 120a then is opened, allowing siphon 120 to open and the resuspension fluid containing the resuspended reagent is flushed from the main chamber/mixing area 116 (and/or area 115) to waste chamber 124 via siphon 120. See FIG. 3L.

Next, a colorimetric solution can be placed in inlet area 108a (FIG. 3M), and held therein. It is thereafter transferred to chamber 108, then on to the main chamber 112 and mixing area 116, via rotation of the disc (FIG. 3N). While in the mixing area, the colorimetric solution mixes with the bead for a predetermined period of time, in some embodiments, 5 minutes of mixing and data collection (and any range from 1-20+ minutes, and ranges therebetween). A colorimetric signal can be collected after a particular period of time, e.g., once every 10-30 seconds, and even up to a minute or more (and ranges therebetween), for the total mixing/data collection (e.g., 1-20+ minutes, and ranges therebetween).

Thereafter, or during mixing, or during mixing intervals, a colorimetric signal is produced by the colorimetric solution/bead interaction, and can be measured via a device for measuring such signals (well known in the art). See FIG. 3O.

Figure 8A:
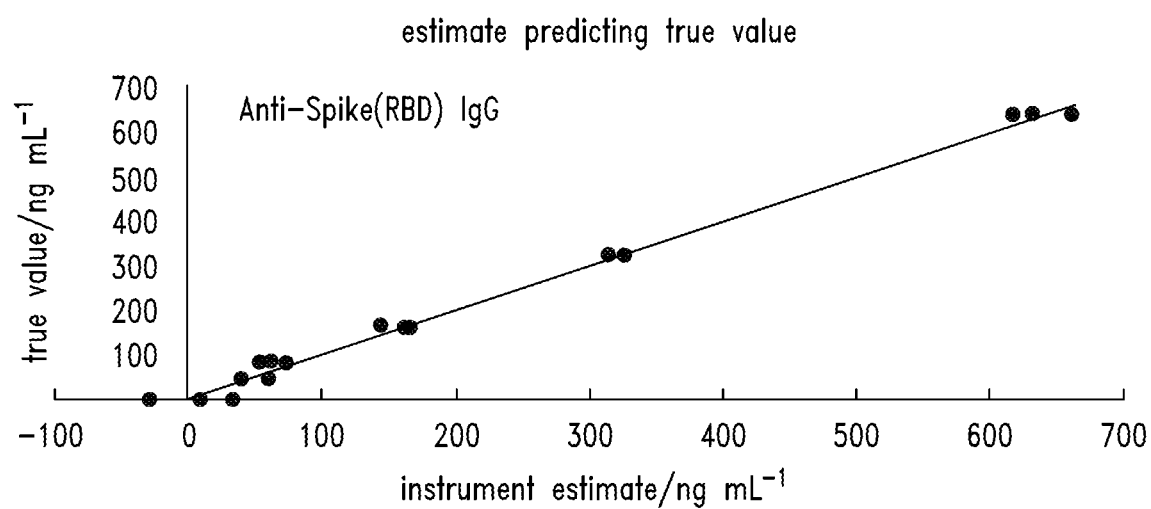
FIG. 8A is a graph illustrating Spike (RBD) concentration predicted for an assay device/system, according to some embodiments.
Figure 8B:
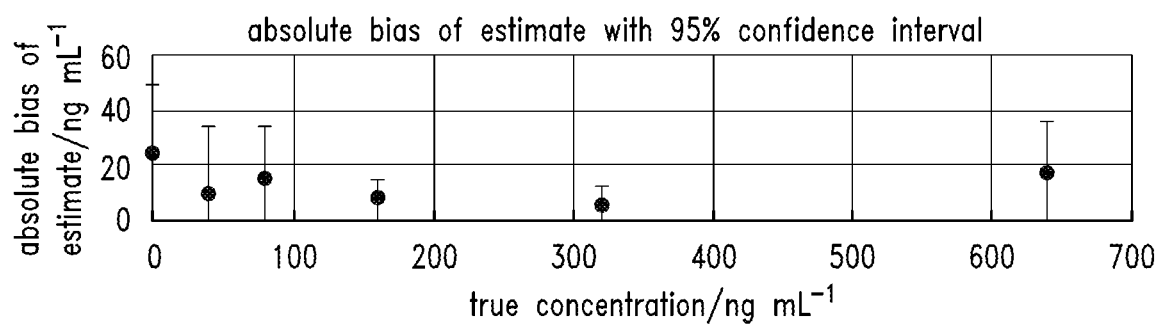
FIG. 8B is a graph illustrating a bias study showing with 95% confidence of anti-spike (RBD) IgG.
Figure 8C:
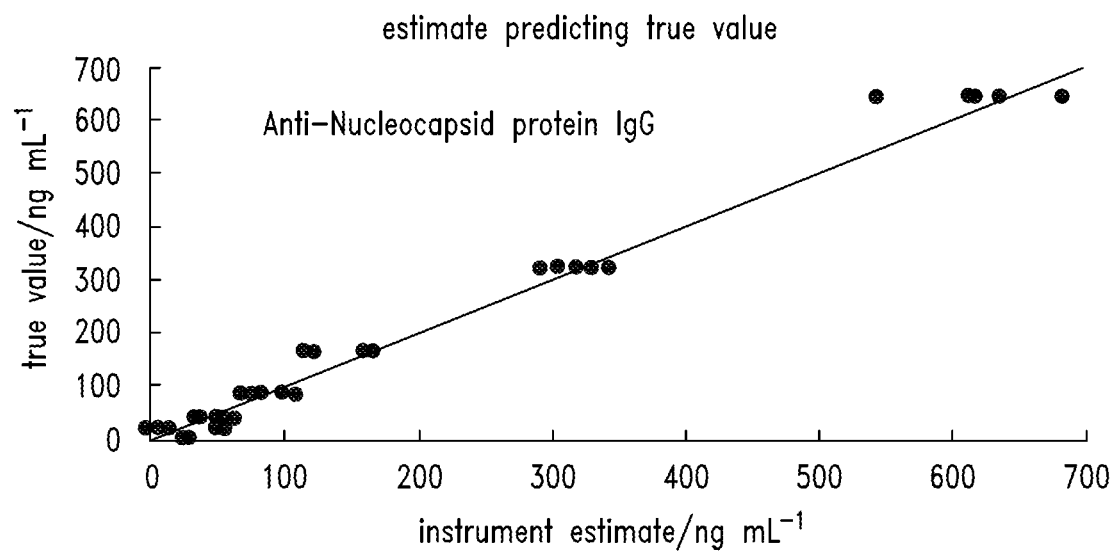
FIG. 8C is a graph illustrating N-protein concentration predicted for an assay device/system, according to some embodiments.
Figure 8D:
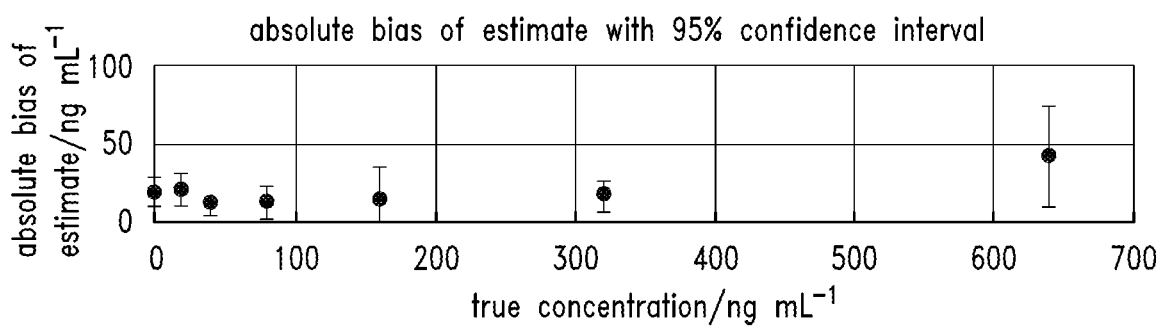
FIG. 8D is a graph illustrating a bias study with 95% confidence of anti-N-protein IgG.

FIG. 8A is a graph illustrating Spike (RBD) concentration predicted for an assay device/system, according to some embodiments;

FIG. 8B is a graph illustrating a bias study showing with 95% confidence of anti-spike (RBD) IgG, of the predicted values of FIG. 8A;

FIG. 8C is a graph illustrating N-protein concentration predicted for an assay device/system, according to some embodiments;

FIG. 8D is a graph illustrating a bias study with 95% confidence of anti-N-protein IgG, of the predicted values of FIG. 8C.

Vial Based Assay Embodiments

As shown in FIGS. 9A-D, some embodiments of the disclosure are directed to a vial-based assay system or kit 900. Such a system or kit, as set out in FIG. 9A, for example, can include a first reaction vial 902, having a first size, shape, and volume of between 0.01-150 ml (and ranges therebetween), including at least one functionalized bead 903 of between 10 µm to 5000 µm (and ranges therebetween) in diameter, the at least one bead 903 including a plurality of binding sites for at least on antigen and a dried or liquid conjugate of the at least one antigen. Optionally, the first vial 902 includes a dried or liquid detergent comprising, for example, at least one of Tween, Brij, and pluronic. The system or kit 900 can also include a second, washing/filter vial 904, having a second size, shape, and volume of between 0.01-150 ml. The second vial 904 can include a barrier 905, which can comprise a filter (for example), which can comprise cellulose, plastic (e.g., nylon); the filter can be any physical barrier that includes a mesh with openings that are less than the diameter of the at least one bead (e.g., during washing). Optionally, a third, waste vial 906, can be included, which may have a third size, shape, and volume, configured for receiving waste (for example). The system or kit 900 can further include a fourth vial 908, having a fourth size, shape, and volume, including a colorimetric reagent and buffer (e.g., powder) containing a reactant to support an enzymatic colorimetric reaction/assay. Optionally, the system or kit 900 can include a fifth vial, having a fifth size, shape, and volume (not shown).

In some embodiments of the disclosure, a vial-based assay method is provided (which can use the system/kit 903, for example, such as detailed above). The method includes adding a sample containing a target comprising at least one of an antigen, molecule, and protein for quantification, 909a, to first vial 902 containing at least one functionalized bead of between 10 µm to 5000 µm in diameter (and ranges therebetween). As noted previously, the at least one bead includes a plurality of binding sites of at least one first antigen, and a dried or liquid conjugate of the at least one first antigen. The first vial optionally includes a dried detergent comprising at least one of Tween, Brij, and pluronic. The method can further include mixing 909b the sample within the first vial 902 for a predetermined period of time including, for example, 5 min (can be between 1 and 20 min and any range therebetween), whereby the antigen and antigen-conjugate can compete for binding sites on the bead 903. Next, removing 909c the sample from vial 902, and transferring 909d the at least one bead from the first vial 902 to a second vial 904 having a barrier 905 component, e.g., a filter. The transfer can be accomplished via a connection of the first vial to the second vial (as shown in 909d). For a washing procedure, the method can include attaching vial 904 to vial 902 which will be used as a waste chamber for the washing procedure; the connection can be via inverting of vial 904 onto vial 902. In this step, the user may use a different vial as waste chamber (e.g., vial 906).

In step 909f, an aqueous solution (e.g., a saline buffer with tween) is added to vial 904, and the vial is placed in a centrifuge and spun for an amount of time, including for example, seconds (e.g., 5 seconds), and in some embodiments, can be between 5-15 seconds, in order to wash the bead 903. More than one washing and discarding of the waste deposited (e.g., in vial 902 or 906) can be done. The at least one bead with captured antigen and antigen-conjugates remains with excess antigen washed off. Note, a positive pressure device or a negative pressure device may also be used for transferring the fluid from the vial including the filter to a/the waste chamber.

In step 909g, the washed bead is retained in vail 904 and the waste solution in the waste vial (for example). Vial 904 is then inverted 909h in vial 908, and the bead(s) 903 is transferred. Thereafter, in 909I, a defined amount of purified water can be added to vial 906, and a colorimetric reaction can occur. The colour change, 909J, is generally proportional to the amount of antigen-conjugate bound to the beads. The vial 908 can then be read using a nanophotometer, spectrophotometer or any other type of standardized reader. The user can also stop the reaction, via addition of, for example, an acid solution (acid solutions can be used to stop TMB colorimetric development). The solution can also be pipetted from the vial into a reader.

Figure 9A:
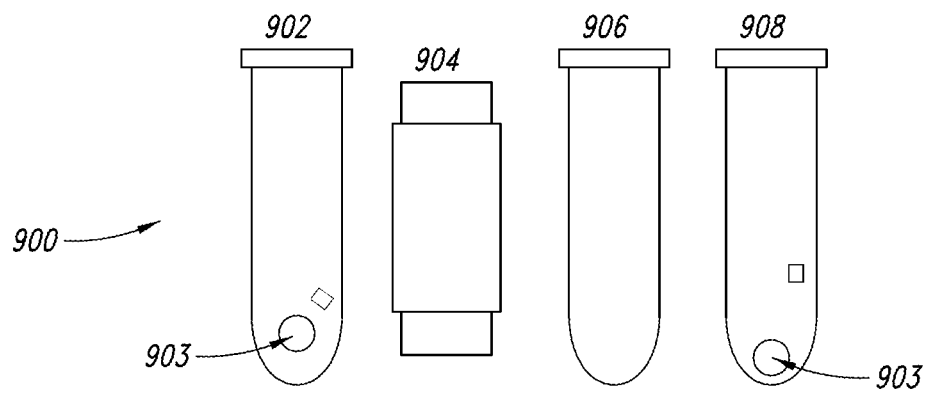
FIG. 9A is a schematic representation of a vial-based, assay system/kit, according to some embodiments of the disclosure.
Figure 9B:
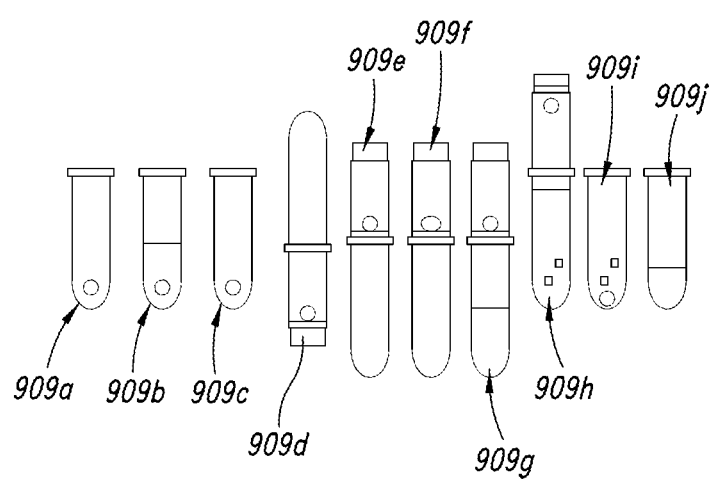
FIG. 9B is a schematic representation of the vial-based system of FIG. 9A, as used in an associated assay method, according to some embodiments of the disclosure.
Figure 9C:
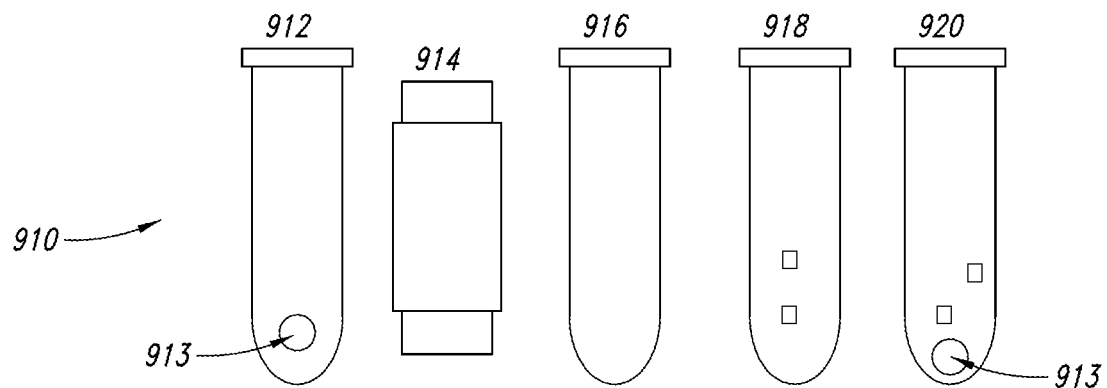
FIG. 9C is a schematic representation of another vial-based, assay system/kit, according to some embodiments of the disclosure.
Figure 9D:
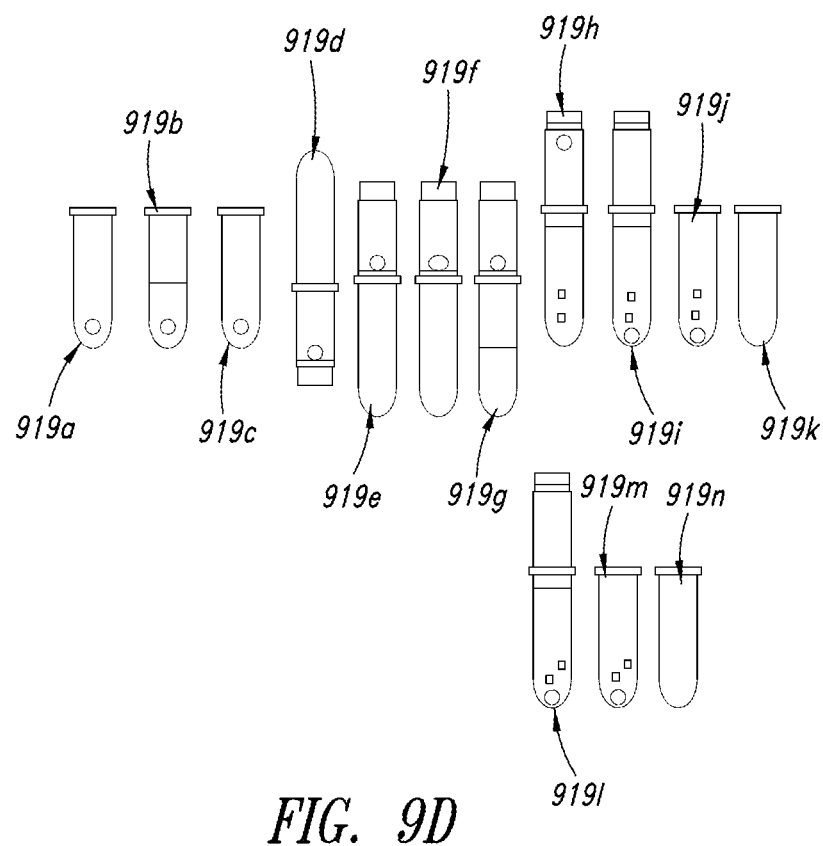
FIG. 9D is a schematic representation of the vial-based system of FIG. 9C, as used in an associated assay method, according to some embodiments of the disclosure.

FIG. 9B illustrates another system or kit 910, according to some embodiments, which can include a first reaction vial 912, having a first size, shape, and volume of between 0.01-150 ml (and ranges therebetween), including at least one functionalized bead 913 of between 10 µm to 5000 µm (and ranges therebetween) in diameter, the at least one bead 913 including a plurality of binding sites for at least on antigen and a dried or liquid conjugate of the at least one antigen. Optionally, the first vial 912 includes a dried or liquid detergent comprising, for example, at least one of Tween, Brij, and pluronic. The system or kit 910 can also include a second, washing/filter vial 914, having a second size, shape, and volume of between 0.01-150 ml (and ranges therebetween, see, e.g., volume ranges for vials, supra). The second vial 914 can include a barrier 915, which can comprise a filter (for example), made of, for example, cellulose or plastic, having a size, or a pore size, configured to retain or hold the at least one bead 913 so as to hold the at least one bead during washing step. Optionally, a third, waste vial 916, can be included, which may have a third size, shape, and volume, configured for receiving waste (for example). The system or kit 910 can further include a fourth vial 918, having a fourth size, shape, and volume, including a colorimetric reagent and buffer (e.g., powder) containing a reactant to support an enzymatic colorimetric reaction/assay. Optionally, the system or kit 910 can include a fifth vial 920, having a fifth size, shape, and volume (which can include a similar size, shape and volumes as with the other vials).

An assay method using system 910 can include the following. First vial 913 is emptied 919*a*. In step 919*b*, a sample containing a target to be quantified (e.g., an antigen, molecule, protein, and the like) is added to vial 912, and mixed for an amount of time (e.g., 5 minutes, and in some embodiments, between 1-30 minutes, and any range therebetween, e.g., 1-5 min, 1-10 min, 1-20 min, 5-10 min, 5-15 min, 5-20 min, 5-25 min, 5-30 min, 10-15 min, 10-20 min, 10-25 min, 10-30 min, 15-20 min, 15-25 min, 15-30 min, 20-25 min, 20-30 min, 25-30 min). As noted above, binding sites on the bead 913 are configured to capture the target in the sample. In 919*c*, after the mixing time, the sample can be removed from vial 912, via, for example, pipetting (thus, vial 912 does not contain liquid, or very little liquid). Thereafter, in step 919*d*, vial 912 without liquid is inverted on vial 914 to transfer the bead(s) to vial 914. In step 919*e*, vial 914 can be attached to a post reaction vial (e.g., 912), for use as a waste chamber for the washing procedure. In this step, the user may use a different vial as waste chamber, e.g., vial 916.

Accordingly, the washing procedure 919*f* is initiated, where an aqueous solution (e.g., a saline buffer with tween) is added to vial 914. The vial 914 is then placed in a centrifuge and spun for an amount of time in order to wash the bead, including for example, seconds (e.g., 5 seconds), and in some embodiments, can be between 5-15 seconds (and ranges therebetween). More than one washing and discarding of the waste deposited in vial 912, if required. The washing procedure results in the bead(s) having captured the target (e.g., antigen, molecule, protein, and the like) with excess antigen having been washed off Note, a positive pressure device or a negative pressure device may also be used for transferring the fluid from the filter to the waste chamber during this step. Accordingly, as shown in 919*g*, the washed bead(s) 913 is kept in vial 914 and the waste solution in the vial below (waste vial).

Thereafter, in 919*h*, 919*i*, vial 914 can be inverted on vial 918 and the bead(s) 913 transferred. In steps 919*j*, 919*k*, a defined amount of purified water can be added to vial 918, and the captured target on the beads then binds to a secondary reagent contained therein (e.g., a secondary antibody). The reaction is run for a definite amount of time (e.g., in some embodiments, between 1-30 minutes, and any range therebetween). In step 919*l*, vial 914 can be inverted on vial 920, and the bead(s) can be transferred. In step 919*m*, a defined amount of purified water can be added to vial 916, and a colorimetric reaction can then take place. The colour change 919*n* is generally proportional to the amount of antigen-conjugate bound to the beads, and accordingly, the vial can be used for reading the colorimetric signal using a nanophotometer, spectrophotometer or any other type of standardized reader. The user can also stop the reaction, via addition of, for example, an acid solution (acid solutions can be used to stop TMB colorimetric development). The solution can also be pipetted from the vial into a reader.

Microfluidic Pneumatic Centrifuge Mixing

As shown in FIGS. 10A-I are directed to provide a pneumatic microfluidic centrifugal mixing apparatus embodiments 1000, which includes a disc 1002, and a plurality of reaction chambers/devices 1004 arranged along a periphery of the disc, each which comprise one or more micro-chambers. Upon spinning of the disc, air/gas within each chamber is compressed thereby establishing a pneumatic pressure (P) within each chamber, and releasing pressure P upon at least one of a change in spin direction of the disc, decreasing the spin velocity of the disc, and stopping the disc, whereby pneumatic energy stored in the disc is released to the main reaction chamber so as to accelerate fluid inside the reaction chamber.

Such embodiments may include one and/or another of (and in some embodiments, a plurality of, in some embodiments, a majority of, and in still further embodiments, all of) the following additional features, functionality, structure, steps, or clarifications, yielding yet further embodiments of the present disclosure:

at least one of a motor, a camera/imager, an LED strobe, a photodiode, a lens, a movement stage configured to move components relative to each other in at least one-dimension, and a ring LED;

two or more of: a motor, a camera, an LED strobe, a photodiode, a lens, a movement stage configured to move components relative to each other in at least one-dimension, and a ring LED;

a motor, a camera, an LED strobe, a photodiode, a lens, a movement stage configured to move components relative to each other in at least one-dimension, and a ring LED; and each chamber includes a sample inlet, a pressure release outlet, a reaction chamber, at least one pneumatic pressure chamber, and a fluid including at least one micro-bead, where the at least one pneumatic pressure chamber comprises at least two pneumatic pressure chambers.

In some embodiments, a micro-fluidic centrifugal mixing method is provided and includes placing a sample in a reaction chamber arranged on a disk, the disk being received in a part of centrifuge apparatus, spinning the disk in a first direction, so as to establish a first pneumatic pressure (P1) within a chamber opposite to the direction of the spin, and at least one of: changing the spin direction, decreasing the spin velocity of the disk, and stopping the disk, so as to release P1. In some embodiments, P1 accelerates fluid inside the reaction chamber.

In some embodiments, a micro-fluidic centrifugal mixing method is provided and includes providing a plurality of chambers arranged along a perimeter of a centrifuge disk, where each chamber comprises a sample inlet, a pressure release outlet, a reaction chamber, at least one pneumatic pressure chambers (PPCs). The method also includes placing a sample in at least one of the chambers via the inlet prior to spinning the disk, wherein each PPC prior to spinning of the disk is at a first pressure P1, and, optionally sealing the chamber (in some embodiments).

Such embodiments may include one and/or another of (and in some embodiments, a plurality of, and in still further embodiments, all of) the following additional features, functionality, structure, steps, or clarifications, yielding yet further embodiments of the present disclosure:

the at least one pneumatic chamber comprising two pneumatic chamber, one each arranged on opposite sides of the reaction chamber;

the reaction chamber includes a fluid including a plurality of microbeads;

spinning the disk in a first direction, so as to establish a second pressure (P2) within a first PPC arranged opposite to the first direction of the spin and a third pressure (P3) within a second PPC of the two PPCs, where, in some embodiments, P2 is greater than P1, and/or P3 is less than P1;

spinning the disk in a single direction only;

spinning the disk in a first direction, and then spinning the disk in an opposite direction;

upon decreasing the spin velocity of the disk, at least a portion of P2 is released into the reaction chamber, such that fluid inside the reaction chamber is accelerated;

upon changing the spin direction of the disk, P2 is released into the reaction chamber, such that fluid inside the reaction chamber is accelerated and pressure within the second PPC begins increasing as the speed of the disk in the opposite direction increases; and upon stopping the disk, P2 is released into the reaction chamber, such that, fluid inside the reaction chamber is accelerated.

As shown in FIG. 10A, a system for microfluidic centrifuge mixing is provided and includes an electric motor 1000J (which may also include an associated motor drive 1000F), a disc 1000H, and a camera 1000C (e.g., CCD or CMOS device with or without optics). In some embodiments, additional hardware includes, for example, at least one of (and in some embodiments a plurality, and in some embodiments, all of: a rotor 1000I, a strobe (e.g., LED) 1000A, a photodiode 1000B, lenses/optics 1000D, movement means 1000E (e.g., motors, actuators, and the like) to move components of the system (e.g., at least one of the camera, the disk), relative to one another (for example), light sources (e.g., LED ring 1000G), as well as a controller 1000K (e.g., computer processor, MyRio). Some of these components enable at least one of connection and synchronism between component as well as the output measurement (e.g., color change of a solution inside of the disc).

In some embodiments of the disclosure, the disc is provided with mixing valves which result in improved mixing for centrifugal microfluidics, leading to, in some embodiments, improved mixing resulting (including, e.g., a 9.5% increase in sensitivity). A sensitivity increase of this amount leads to, in some embodiments, greater reproducibility as well as faster assays. Beads larger than about 1000 μm tend not to mix well without use of the disclosed valves according to some embodiments.

In some embodiments, the systems, devices, and methods impart an effective impulse to fluid upon change of direction of a centrifuge disk, resulting in an acceleration with respect to detection of beads, hence, a greater fluid velocity past an associated detection surface, and hence, more efficient transport of molecules from the fluid to the detection surface.

In some embodiments, a plurality of microchannels and/or microchambers 1004 arranged along or proximate the circumference of the disc (FIG. 10B), which may individually be referred to as a reaction chamber) are provided, with each connected to a mixing chamber without (in some embodiments) a pressure outlet (i.e., a closed system). In such embodiments, as the disk spins and accelerates, air is compressed as the disc spins and accelerates. Upon a change in spin direction, a decrease of spin velocity, or stop of the spin (or, in some embodiments, a subsequent combination of two or more of such actions), stored pneumatic energy is released to each reaction chamber. This generates fluid propulsion inside the reaction chamber, which then results in higher movement of the beads/particles.

Figure 10C:
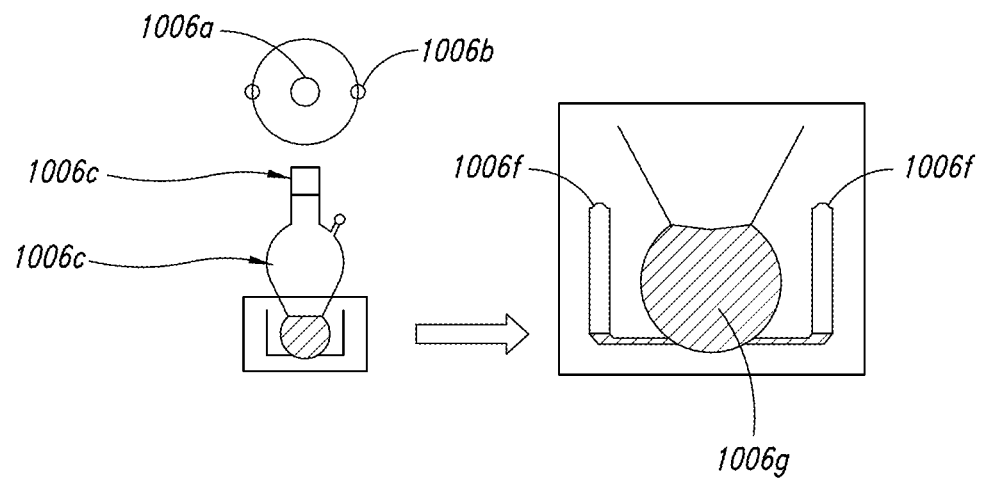

FIG. 10C shows an example of a system/device according to some embodiments. A sample mixing chamber with 1006A centre of rotation of the disk, and a 1006b direction of rotation of the disk, 1006c an air pressure release outlet, 1006d a sample insertion inlet, 1006e a reaction chamber, 1006f pneumatic pressure chambers, and 1006g a reservoir containing a fluid with microbeads (the pressure valves are not drawn to scale for better visualization).

Figure 10D:
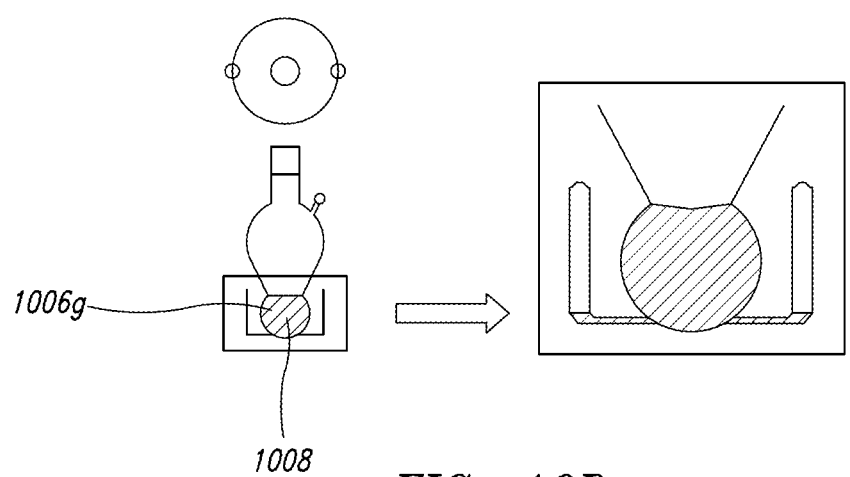
Figure 10E:
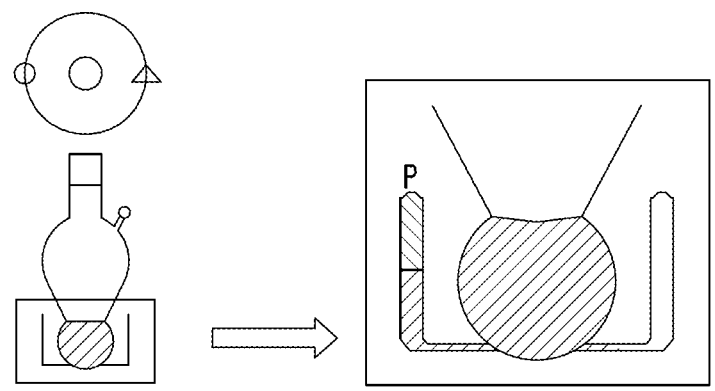
Figure 10F:
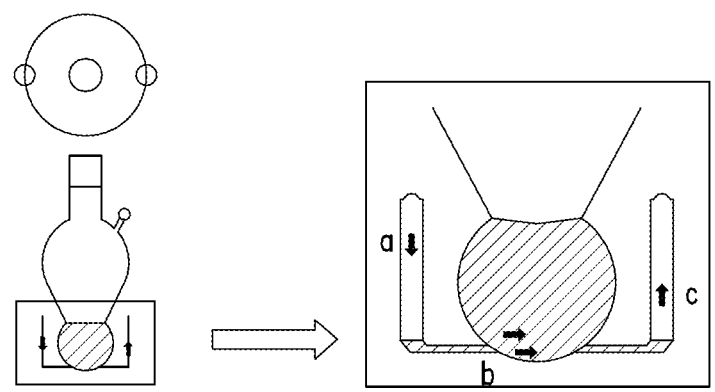

In some embodiments, an example of a sequence showing pneumatic pressure mixing is provided (via valves according to some embodiments); please note, the components of the fluid levelling device in FIGS. 10C-H are the same as those shown and described in FIG. 10C. Specifically, a sequence of spin runs from FIGS. 10D-G. In FIG. 10D (for structure, reference FIG. 10C) a sample 1008 is placed in the reaction chamber with or without a spin, and the disk is stopped. Pressure on the closed system channels (pneumatic pressure chambers) is low. In FIG. 10E, the disc is spun in an anti-clockwise direction, which builds pneumatic pressure (P) at the closed channel or chamber opposite to the direction of the spin. In FIG. 10F, the disk stops and/or changes direction, thereby releasing pressure from the pneumatic pressure channel (a) (the left channel) to the reaction chamber (b).

Figure 10G:
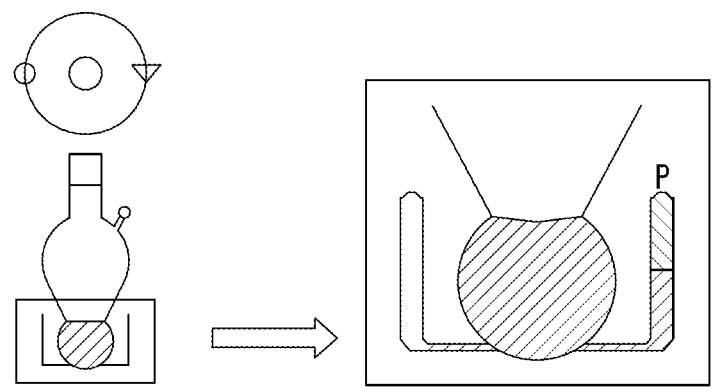
Figure 10H:
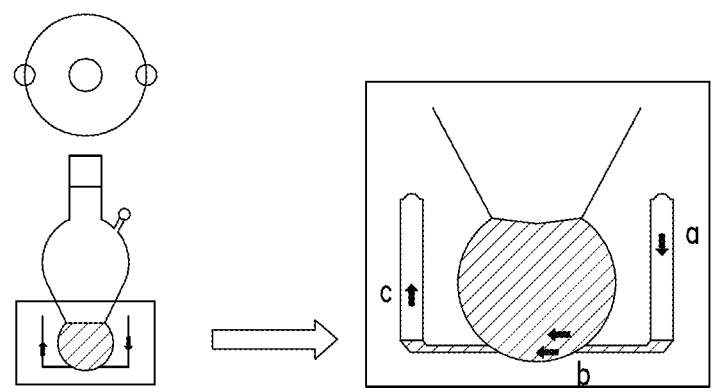

In FIG. 10G, a change in spin direction (e.g., from counter-clockwise to clockwise) increases/builds-up pressure in the other pneumatic pressure channel (e.g., on the opposite side of the spin direction, here the right channel). FIG. 3H, the disk stops and/or changes direction and the pressure is released from the "right" pressure channel to the reaction chamber.

Example

Figure 10I:
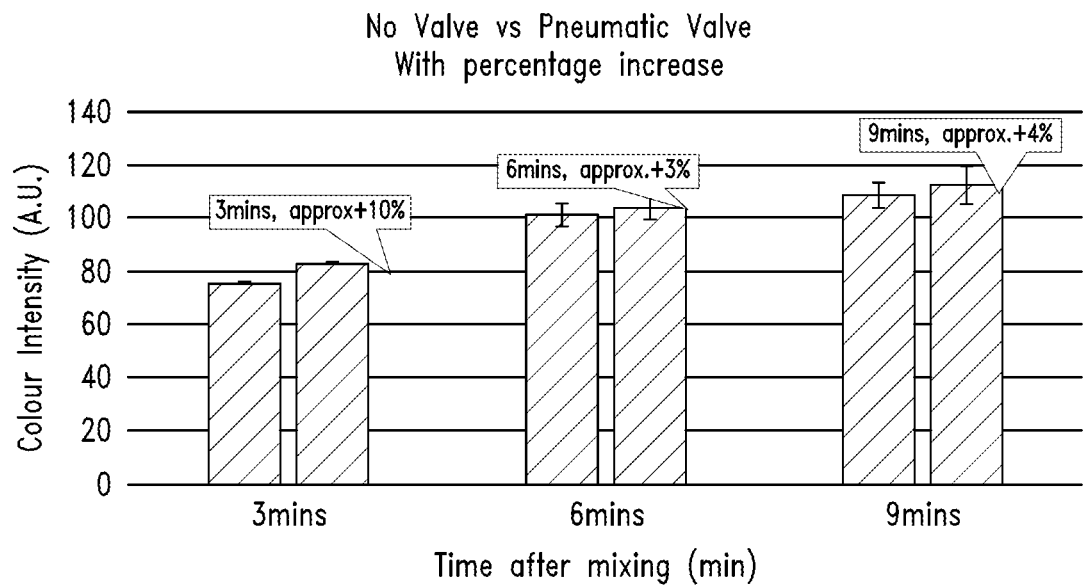

An increase of approximately 9.5% in the rate of change of color in the detection of progesterone concentration in milk using methods and systems according some of the embodiments of the present disclosure (and in the current example, within the first 3 minutes). FIG. 10I shows the control (no use of pneumatic mixing valves) and pneumatic valves values (three sets of data, the right column for each set representing results using the pneumatic centrifuge mixing embodiments).

Fluid Height Control Device/Method

The precision and reproducibility of vibrational spectroscopy in open channel microfluidics (or liquid samples) is highly dependent on the reproducibility of a working distance between a probe and fluid. Furthermore, vibrational spectroscopy using high laser power can affect the rate of evaporation of the fluid, resulting in a change in the height of the fluid during experiment, which can affect results.

Accordingly, in some embodiments of the present disclosure, a simple, system and method to retain fluid at a particular height in, for example, a microfluidic system (e.g., a chip), which can be referred to as fluid height control. Accordingly, in some embodiments:

such a microfluidic chip includes a central measurement chamber (open), and a plurality of open outputs (in some embodiments, two open outputs);

fluid in the centre is held without a meniscus (i.e., it is flat) due to the surface tension, with a meniscus being formed in the output ports;

all chambers are connected; and different materials can be used according to suitability for specific functionalities;

In some embodiments, a microfluidic fluid levelling chip is provided and includes a housing having a first upper surface and a second lower surface, a central chamber having a central-chamber diameter (CCD) and an opening on or above the first surface, and having a central chamber height (CCH) from a bottom of the chamber to the first opening (where, in some embodiments, CCD is greater than CHH). A pair of side chambers are provided and arranged in an opposed relationship with the central chamber, where each side chamber includes a side-chamber diameter (SCD) and corresponding opening on or above the first surface. Each side chamber also includes a side chamber height (SCH) from a bottom of the respective side chamber to the first surface. The chip also includes a pair of fluid communication channels, one each corresponding to a respective one of the pair of side chambers and arranged to fluidly connect each side chamber to the central chamber, each channel including a channel width (CW) and a channel height (CH). In some of the above embodiments, the SCD is smaller than the CCD. In some embodiments, the central chamber, side chambers and fluid communication channels are configured such that:

- an amount of fluid arranged among the chambers results in a surface of the fluid in the central chamber being substantially flat and substantially lacking a meniscus,
- the height of the fluid in each side chamber being greater than the height of the fluid within the central chamber, and
- the surface of the fluid in each side chamber includes a meniscus.

Figure 11A:
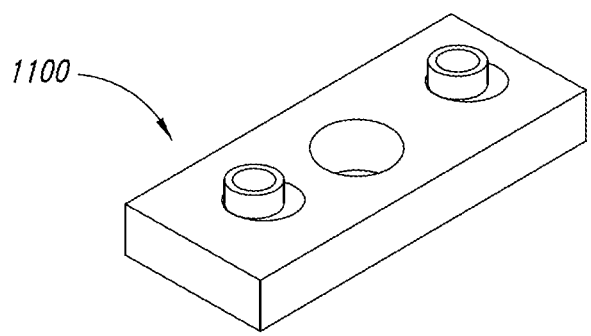
FIGS. 11A-E are various illustrations of a microfluidic, fluid levelling device, including an example use thereof (see FIG. 11E), according to such embodiments of the disclosure.

FIGS. 11A-1B, is an example of a fluid levelling microchip 1100 according to some embodiments, illustrating a model (FIG. 11A), and a reveal image (FIG. 11B, e.g., x-ray), illustrating a view of the chip being fluid filled (darker color). FIG. 11C, illustrates a lateral/side view of the chip 1100 according to some embodiments. As shown, 1102a corresponds to an input where the fluid is initially placed to fill up a detection chamber 1102b. Note, in the illustrated embodiment, there is no formation of a meniscus. The height at which the fluid rises at the input 1102h0, is higher than the height of the fluid 1102h1 in the detection chamber 1102b.

Figure 11B:
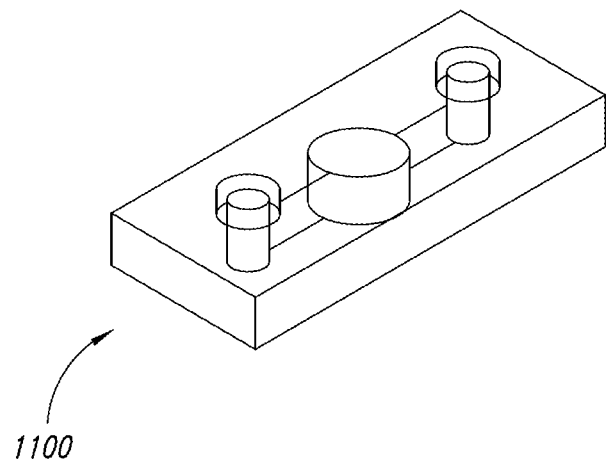
Figure 11C:
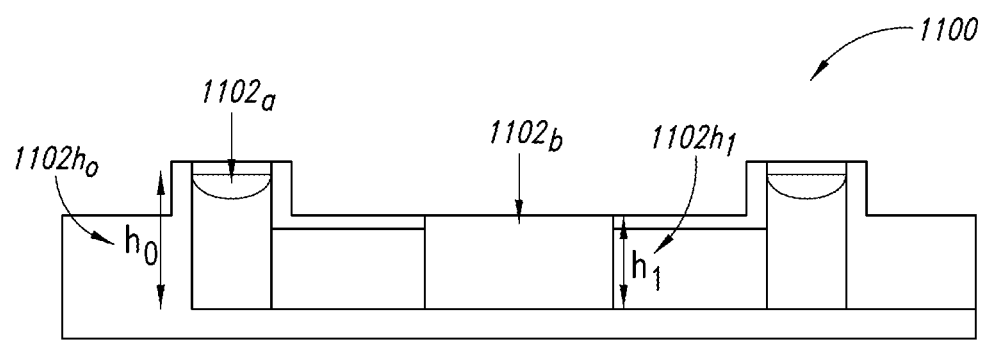
Figure 11D:
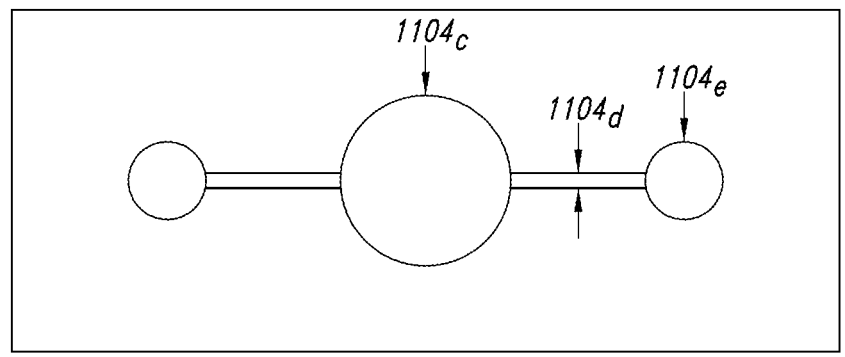

FIG. 11D, is a top view of a chip according to some embodiments (which includes that shown in FIG. 11A-B). As shown, 1104c is the central chamber, and 1104e is a fluid input chamber. Channels 1104d connect input and detection chambers. These channels and their associated decrease in radius (relative to either or both of the input chamber 1104e and detection/central chamber, associated with 1104c, increase the surface area to volume ratio, allowing the surface tension of the liquid to hold the fluid in a flat position in the detection/central chamber area.

Example

Figure 11E:
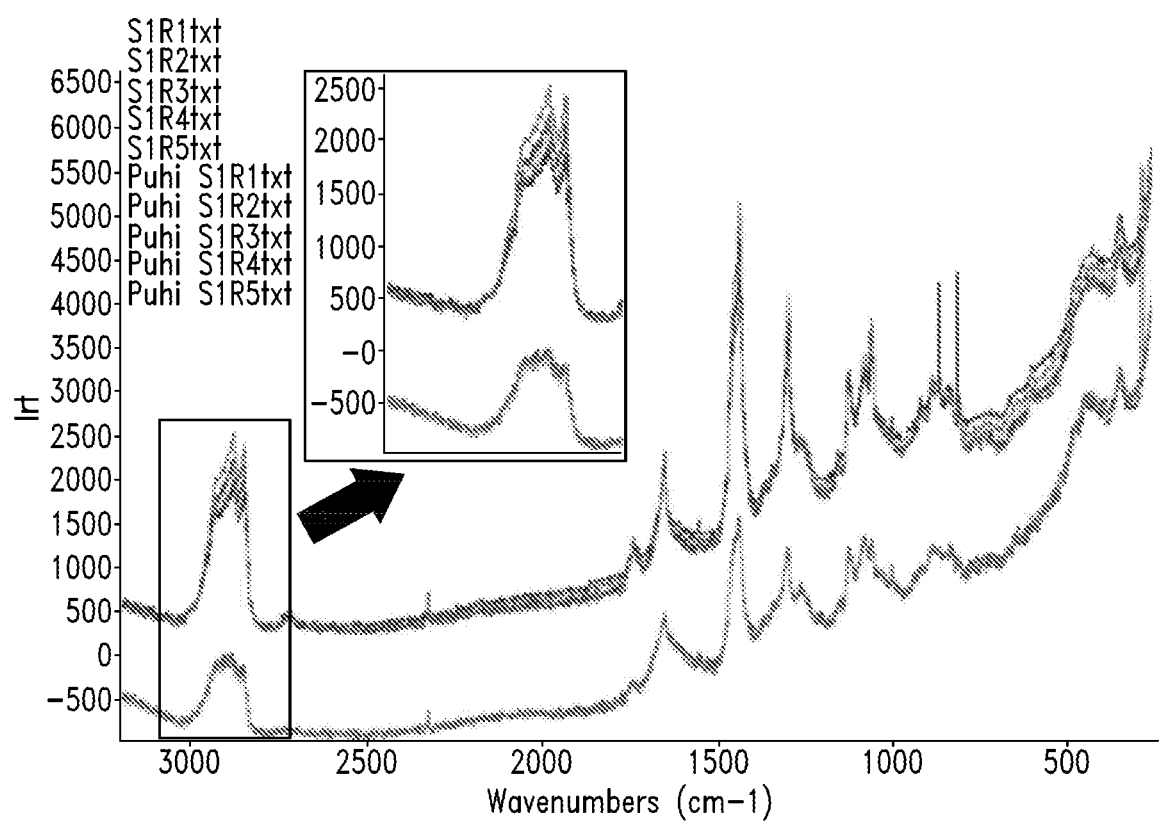

FIG. 11E illustrates the Raman spectroscopy using a fluid-height control embodiment (which may also be referred to as the "Levelling Chip") versus the use of a common/regular chip to hold the fluid for Raman measurements. As shown, Raman Spectroscopy of Silver Top (high fat content) milk. The spectra measured in each type of chip (present embodiment, vs. prior commercial chip) were stacked with spectra results of a regular method/device for better visualisation. Accordingly, the top set of spectra represents different trials using a regular platform/chip to measure the Raman spectra (in which the presence of meniscus was evident). The bottom set of spectra was taken using a chip according to the fluid-height control embodiment, which illustrates higher reproducibility. The CH stretch (seen in the black box) is one of the important parts of the spectra of milk used for fat quantification.

Other Considerations for the Disclosed Inventions and Embodiments

While various inventions and embodiments thereof have been described and illustrated herein, those of ordinary skill in the art will readily envision a variety of other means and/or structures for performing the function, and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, steps, and configurations described herein are meant to be merely an example and that the actual parameters, dimensions, materials, steps, and configurations will depend upon the specific application or applications for which the inventive teachings is/are used. Those skilled in the art will recognize, or be able to ascertain using no more than routine experimentation, many equivalents to the specific inventive embodiments described herein. It is therefore to be understood that the foregoing embodiments are presented by way of example only and that, within the scope of claims supported by the subject disclosure and equivalents thereto, and inventive embodiments may be practiced otherwise than as specifically described and claimed. Inventive embodiments of the present disclosure are directed to each individual feature, device, system, article, material, kit, step, function/functionality, and method described herein. In addition, any combination of two or more such features, devices, systems, articles, materials, kits, steps, functions/functionality, and methods, if such features, systems, articles, materials, kits, steps, functions/functionality, and methods are not mutually inconsistent, is included within the inventive scope of the present disclosure, and considered embodiments.

Embodiments disclosed herein may also be combined with one or more features, as well as complete systems, devices, and/or methods, including those between different inventions and associated embodiments, to yield yet new inventions and other embodiments. Moreover, some claimed embodiments, of one and/or another of the disclosed inventions, may be distinguishable from the prior art by specifically lacking one and/or another feature disclosed in the particular prior art reference(s); i.e., claims to such embodiments may be distinguishable from the prior art by including one or more negative limitations.

Also, as noted, various inventive concepts may be embodied as one or more methods, of which one or more examples have been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments. Thus, any flowchart and block diagrams of the present disclosure are examples of architecture, functionality, and operations, of at least some of the embodiments of systems, devices, and methods supported herein.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The terms "can" and "may" are used interchangeably in the present disclosure, and indicate that the referred to element, component, structure, function, functionality, objective, advantage, operation, step, process, apparatus, system, device, result, or clarification, has the ability to be used, included, produced, or otherwise stand for the proposition indicated in the statement for which the term is used (or referred to).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The terms "can" and "may" are used interchangeably (generally) in the present disclosure, and indicate that the referred to element, component, structure, function, functionality, objective, advantage, operation, step, process, apparatus, system, device, result, or clarification, has the ability to be used, included, or produced, or otherwise stand for the proposition indicated in the statement for which the term is used (or referred to).

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. An assay device configured for arrangement on a disc, and configured to process an individual sample, the assay device positioned along a periphery of the disc at a predetermined radius in a spaced apart arrangement, the assay device comprising:
    a plurality of chambers each configured to receive one or more fluids via a respective inlet area;
    a resuspension chamber including a scaffold for drying and retaining at least one reagent;
    a main chamber comprising a mixing area;
    at least one bead;
    and
    a bead stabilization area, separate from the mixing area and main chamber, wherein the bead stabilization area:
        is arranged between an end of the mixing area and an outer edge of the disc,
        is in fluid communication with the mixing area and includes an opening for receiving the at least one bead from the mixing area, and
        is sized and shaped so as to contain the at least one bead when at rest so as to remove it from the mixing area.

2. The device of claim 1, wherein the plurality of chambers comprise at least a first peripheral chamber, a second peripheral chamber, and a third peripheral chamber.

3. The device of claim 1, wherein each of the plurality of chambers include a corresponding inlet area.

4. The device of claim 3, wherein each inlet area is configured to flow or otherwise transfer a fluid to a respective chamber via a microfluidic channel.

5. The device of claim 1, wherein the plurality of chambers comprise at least two of:
    a first peripheral chamber having an associated first inlet area, the first inlet area in fluid communication with the first peripheral chamber via a first microchannel, wherein fluid received in the first inlet area flows into the first peripheral chamber;
    a second peripheral chamber having an associated second inlet area, the second inlet area in fluid communication with the second peripheral chamber via a second microchannel, wherein fluid received in the second inlet area flows into the second peripheral chamber;
    and a third peripheral chamber having an associated third inlet area, the third inlet area in fluid communication with the third peripheral chamber via a third microchannel, wherein fluid received in the third inlet area flows into the third peripheral chamber.

6. The device of claim 1, wherein the resuspension chamber is in fluid communication with at least one other of the plurality of chambers via an associated microfluidic channel.

7. The device of claim 1, wherein the scaffold material comprises a mesh.

8. The device of claim 7, wherein the mesh configured as a geometric shape.

9. The device of claim 7, wherein the geometric shape comprises a circular disc between 1-6 mm in diameter.

10. The device of claim 7, wherein the mesh includes a mesh or pore size selected from the group consisting of between: 10-250 µm, between 10-20 µm, between 20-40 µm, 40-60 µm, 60-80 µm, 80-100 µm, 100-120 µm, 120-140 µm, 140-160 µm, 160-180 µm, 180-200 µm, 200-220 µm, 220-240 µm, 240-250 µm.

11. The device of claim 1, wherein the mixing area is arranged distally to the main chamber towards an edge of the disc.

12. The device of claim 11, wherein the mixing chamber includes one or more pre-stored reagents.

13. The device of claim 1, wherein the mixing chamber includes a detection window.

14. The device of claim 1, wherein bead stabilization area stabilizes the at least one bead during measurements.

15. The device of claim 1, wherein the bead includes at least one capture reagent establishing a plurality of binding sites thereon.

16. The device of claim 15, wherein the capture reagent of the bead comprises at least one of one or more antibodies and antigens.

17. The device of claim 15, wherein the reagent covers a percentage of the surface of the at least one bead.

18. The device of claim 1, wherein the at least one bead includes a diameter of between 100 µm-2500 µm.

19. The device of claim 1, further comprising a first siphon channel and an associated valve configured with a size and length to at least one of time and mix a dried reagent for resuspension of the dried reagent in the resuspension chamber.

20. The device of claim 1, further comprising at least one siphon channel.

21. The device of claim 20, wherein the siphon channel includes at least one microfluidic capillary valve being in fluid communication with the resuspension chamber and the main chamber.

22. The device of claim 1, further comprising a microfluidic pressure release capillary valve in communication with the main chamber.

23. The device of claim 20, further comprising a second siphon channel and an associated valve configured with a size and length to provide at least one of a timing and mixing in the main chamber.

24. The device of claim 23, wherein the second siphon includes at least one microfluidic capillary valve.

25. The device of claim 1, further comprising a waste chamber in communication with the main chamber via at least one siphon.

26. The device of claim 25, further comprising a pressure release outlet m fluid communication with the waste chamber via a microfluid channel.

27. The device of claim 1, further comprising at least one microfluidic capillary valve including a dried hydrophobic material configured to decrease wettability at a specific area such that fluid flow/transitions via the capillary valve is based on a rotational speed of the disc.

28. The device of claim 27, wherein each capillary valve includes at least one of a surface modification of a contact angle at an entrance thereof so as to prevent fluid uncontrolled bridging of the capillary valve, and an increase in pressure to open the valve.

* * * * *